United States Patent
Kikuchi et al.

(10) Patent No.: US 7,741,393 B2
(45) Date of Patent: Jun. 22, 2010

(54) ORGANIC SILICON-BASED COMPOUND AND METHOD OF PRODUCING THE SAME

(75) Inventors: Taketoshi Kikuchi, Ibaraki (JP); Atsushi Higo, Toyonaka (JP); Hideaki Awa, Ibaraki (JP); Kunihito Miyake, Yamatokoriyama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 851 days.

(21) Appl. No.: 10/592,501

(22) PCT Filed: Mar. 10, 2005

(86) PCT No.: PCT/JP2005/004719

§ 371 (c)(1), (2), (4) Date: Sep. 12, 2006

(87) PCT Pub. No.: WO2005/087781

PCT Pub. Date: Sep. 22, 2005

(65) Prior Publication Data

US 2007/0203275 A1   Aug. 30, 2007

(30) Foreign Application Priority Data

Mar. 16, 2004   (JP) .............................. 2004-074116

(51) Int. Cl.
*C08K 5/5419* (2006.01)
*C07F 7/02* (2006.01)

(52) U.S. Cl. ................... 524/264; 524/267; 524/269; 556/451; 556/480; 556/481

(58) Field of Classification Search ............ 524/264, 524/267, 269; 556/451, 480, 481
See application file for complete search history.

(56) References Cited

U.S. PATENT DOCUMENTS 3,440,266 A * 4/1969 Wu .......................... 556/433
5,668,204 A * 9/1997 Meier et al. ................. 524/267
2004/0127070 A1 * 7/2004 Teff et al. .................... 438/787

FOREIGN PATENT DOCUMENTS

JP   2001-247758   9/2001
JP   2005-232258   9/2005

* cited by examiner

*Primary Examiner*—Milton I Cano
*Assistant Examiner*—John Uselding
(74) *Attorney, Agent, or Firm*—Foley & Lardner LLP

(57) ABSTRACT

Provided are an organic silicon compound of the following formula (I):

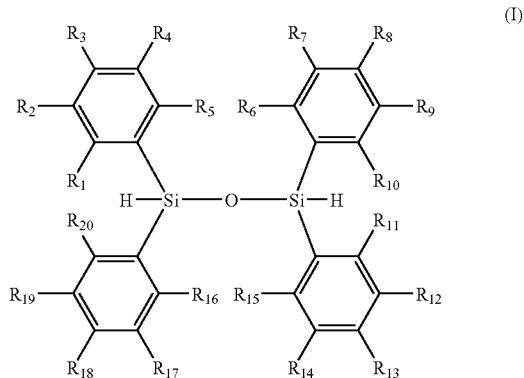

(wherein, $R_1$ to $R_{20}$ represent each independently alkyl, alkoxy, aryloxy, cycloalkyl, alkylcycloalkyl, aryl, dialkylamino or the like, and the aryloxy and aryl may be substituted with a substituent selected from the group consisting of alkyl, alkoxy and alkoxyalkyl.) which can be used for suppression of coloration and thermal deterioration of an organic material in molding, and an organic material composition containing the organic silicon compound and a method of producing the organic silicon compound.

5 Claims, No Drawings

ORGANIC SILICON-BASED COMPOUND AND METHOD OF PRODUCING THE SAME

TECHNICAL FIELD

The present invention relates to a novel organic silicon compound, a method of producing the same, and an organic material composition containing an organic silicon compound and an organic material.

BACKGROUND ART

Organic materials such as thermoplastic resins, thermosetting resins, natural or synthetic rubbers, mineral oils, lubricants, adhesives, paints and the like deteriorate due to an action of heat, oxygen and the like in production, in processing and in use, accompanied by decrease in strength property, change of flowability, coloration, decrease in surface physical property, and the like of the organic materials ascribable to a phenomenon such as molecule cut and molecule crosslinking, leading to remarkable deterioration of commercial value in some cases.

A polycarbonate which is one of thermoplastic resins is used generally in electric device housings, optical lenses, and building materials such as windowpane and the like because of excellent impact resistance, transparency, dimension stability and the like.

In patent document 1, as a stabilizer for a polycarbonate having a main repeating unit represented by the following formula:

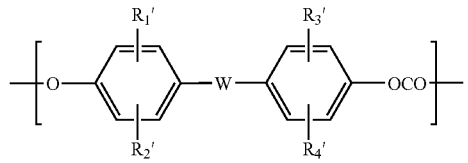

(wherein, $R_1'$, $R_2'$, $R_3'$ and $R_4'$ represent each independently a hydrogen atom, alkyl group having 1 to 10 carbon atoms, aralkyl group or aryl group, and W represents an alkylidene group, cycloalkylene group, alkylene group substituted with an aryl group, oxygen atom, sulfur atom, sulfoxide group or sulfone group.), suggested is a silane type stabilizer of the following formula (A):

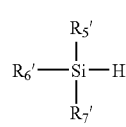

(A)

(wherein, $R_5'$ to $R_7'$ represent each independently a hydrogen atom, alkyl group having 1 to 20 carbon atoms, alkoxyl group having 1 to 20 carbon atoms or aryl group having 6 to 20 carbon atoms, or a silyl group of the following formula (B):

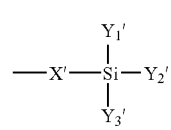

(B)

{wherein, X' represents a single bond, oxygen atom, sulfur atom or alkylene group having 1 to 10 carbon atoms. $Y_1'$ to $Y_3'$ represent each independently a hydrogen atom, alkyl group having 1 to 20 carbon atoms, alkylsilyl group having 1 to 20 carbon atoms, alkylsiloxy group having 1 to 20 carbon atoms, aryl group having 6 to 20 carbon atoms optionally having a substituent, arylsilyl group having 6 to 20 carbon atoms, arylsiloxy group having 6 to 20 carbon atoms or siloxanyl group.}).

Patent document 1: JP-A No. 2001-247758

DISCLOSURE OF THE INVENTION

The present inventors, however, have obtained a finding that when the silane type stabilizer (A) described in patent document 1 is used, an effect of preventing coloration, an effect of preventing thermal degradation and an effect of suppressing generation of gel of organic materials such as polyesters, polyolefins, natural rubber, synthetic rubber, mineral oils, lubricants, adhesives and the like typically including a polycarbonate in molding at high temperatures are not necessarily sufficient.

According to the organic silicon compound of the present invention, coloration, thermal degradation and generation of fish eye gel of organic materials such as a polycarbonate and the like in molding at high temperatures are suppressed.

Namely, a first embodiment of the present invention relates to an organic silicon compound of the following formula (I) (hereinafter, referred to as organic silicon compound of the present invention):

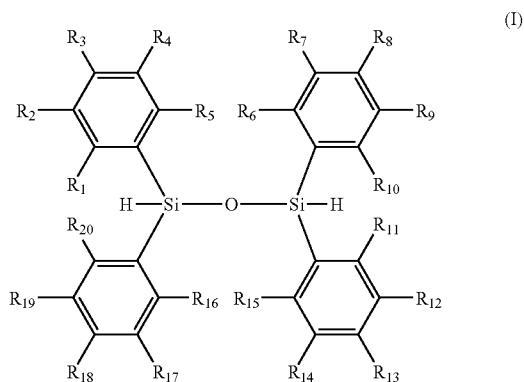

(I)

(wherein, $R_1$ to $R_{20}$ represent each independently a hydrogen atom, alkyl group having 1 to 30 carbon atoms, alkoxyl group having 1 to 30 carbon atoms, alkoxyalkyl group having 2 to 30 carbon atoms, aryloxy group having 6 to 18 carbon atoms, aryl group having 6 to 18 carbon atoms, cycloalkyl group having 5 to 8 carbon atoms, alkylcycloalkyl group having 6 to 20 carbon atoms, alkylthio group having 1 to 30 carbon atoms or dialkylamino group having 2 to 30 carbon atoms.

Here, $R_1$ to $R_{20}$ do not all represent a hydrogen atom simultaneously, and 1 to 3 hydrogen atoms in the aryloxy group having 6 to 18 carbon atoms and the aryl group having 6 to 18 carbon atoms may be substituted by 1 to 3 substituents selected from the group consisting of alkyl groups having 1 to 30 carbon atoms, alkoxyl groups having 1 to 30 carbon atoms and alkoxyalkyl groups having 2 to 30 carbon atoms.)

A second embodiment of the present invention relates to a method of producing the organic silicon compound of the formula (I) described above, comprising reacting a phenyl metal compound of the following formula (III) to (VI) with a substituted silicon compound of the following formula (VII), then, hydrolyzing the resultant reaction product, and if necessary, further condensing the product:

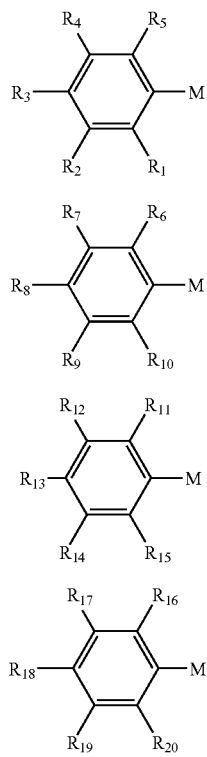

(in the formulae (III) to (VI), M represents MgX or Li, X represents a halogen atom, and $R_1$ to $R_{20}$ are as defined above. Here, $R_1$ to $R_{20}$ do not all represent a hydrogen atom simultaneously.)

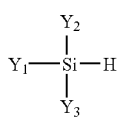

(wherein, $Y_1$ to $Y_3$ represent each independently a halogen atom or alkoxyl group.).

Further, a third embodiment of the present invention relates to an organic material composition comprising an organic material and the organic silicon compound of the formula (I) described above, wherein the weight ratio of the organic material to the organic silicon compound is 100:0.0001 to 100:10 (hereinafter, referred to as organic material composition of the present invention).

BEST MODES FOR CARRYING OUT THE INVENTION

The present invention will be illustrated in detail below.

The organic silicon compound of the formula (I) according to the first embodiment of the present invention will be described below.

The alkyl group represented by $R_1$ to $R_{20}$ in the formula (I) includes alkyl groups having 1 to 30 carbon atoms such as, for example, a methyl group, ethyl group, n-propyl group, i-propyl group, n-butyl group, i-butyl group, sec-butyl group, t-butyl group, t-pentyl group, i-octyl group, t-octyl group, 2-ethylhexyl group and the like. Of the alkyl groups having 1 to 30 carbon atoms, a methyl group, ethyl group and t-butyl group are preferable.

The alkoxyl group represented by $R_1$ to $R_{20}$ includes alkoxyl groups having 1 to 30 carbon atoms such as, for example, a methoxy group, ethoxy group, n-propyloxy group, i-propyloxy group, n-butoxy group, i-butoxy group, sec-butoxy group, t-butoxy group, t-pentyloxy group, i-octyloxy group, t-octyloxy group, 2-ethylhexyloxy group and the like. Of the alkoxyl groups having 1 to 30 carbon atoms, a methoxy group and ethoxy group are preferable.

The alkoxyalkyl group represented by $R_1$ to $R_{20}$ includes alkoxyalkyl groups having 2 to 30 carbon atoms such as, for example, a methoxymethyl group, ethoxymethyl group, n-propoxymethyl group, i-propoxymethyl group, n-butoxymethyl group, i-butoxymethyl group, sec-butoxymethyl group, t-butoxymethyl group, t-pentyloxymethyl group, i-octyloxymethyl group, t-octyloxymethyl group, 2-ethylhexyloxymethyl group, methoxyethyl group, ethoxyethyl group, n-propoxymethyl group, i-propoxymethyl group, n-butoxyethyl group, i-butoxyethyl group, sec-butoxyethyl group, t-butoxyethyl group, t-pentyloxyethyl group, i-octyloxyethyl group, t-octyloxyethyl group, 2-ethylhexyloxyethyl group and the like.

The alkylthio group represented by $R_1$ to $R_{20}$ includes, for example, a methylthio group, ethylthio group, n-propylthio group, i-propylthio group, n-butylthio group, i-butylthio group, sec-butylthio group, t-butylthio group, t-pentylthio group, i-octylthio group, t-octylthio group, 2-ethylhexylthio group and the like.

The aryl group represented by $R_1$ to $R_{20}$ includes monocyclic to tricyclic aryl groups (6 to 18 carbon atoms) optionally substituted with 1 to 3 substituents selected from the group consisting of alkyl groups having 1 to 3 carbon atoms and alkoxy groups having 1 to 3 carbon atoms such as, for example, a phenyl group, 2-methylphenyl group, 3-methylphenyl group, 4-methylphenyl group, 2-methoxyphenyl group, 3-methoxyphenyl group, 4-methoxyphenyl group, 2-methoxyphenyl group, 3-methoxyphenyl group, 4-methoxyphenyl group and the like.

The aryloxy group represented by $R_1$ to $R_{20}$ includes aryloxy groups having 6 to 18 carbon atoms such as, for example, a phenoxy group, 2-methylphenyloxy group, 3-methylphenyloxy group, 4-methylphenyloxy group, 2-t-butylphenyloxy group, 3-t-butylphenyloxy group, 4-t-butylphenyloxy group, 2,4-dimethylphenyloxy group, 2,6-dimethylphenyloxy group, 2,4-di-t-butylphenyloxy group, 2,6-di-t-butylphenyloxy group, 2,4,6-trimethylphenyloxy group, 2,4,6-tri-t-butylphenyloxy group, 2-methoxyphenyloxy group, 3-methoxyphenyloxy group, 4-methoxyphenyloxy group and the like. Of the aryloxy groups having 6 to 18 carbon atoms, a phenoxy group is preferable.

The cycloalkyl group represented by $R_1$ to $R_{20}$ includes cycloalkyl groups having 5 to 8 carbon atoms such as, for example, a cyclopentyl group, cyclohexyl group, cycloheptyl group, cyclooctyl group and the like.

The alkylcycloalkyl group represented by $R_1$ to $R_{20}$ includes alkylcycloalkyl groups having 6 to 20 carbon atoms such as, for example, a 1-methylcyclopentyl group, 1-methylcyclohexyl group, 1-methyl-4-i-propylcyclohexyl group and the like.

The dialkylamino group represented by $R_1$ to $R_{20}$ includes, for example, a dimethylamino group, diethylamino group, di-n-propylamino group, di-i-propylamino group, di-n-butylamino group, di-i-butylamino group, di-sec-butylamino group, di-t-butylamino group, di-t-pentylamino group, di-i-octylamino group, di-t-octylamino group, di-2-ethylhexylamino group and the like.

The organic silicon compound of the present invention can be produced by reacting a phenyl metal compound of the formula (III) to (VI) with a substituted silicon compound of the formula (VII), then, hydrolyzing the resultant reaction product, and if necessary, further condensing the product.

The above-mentioned reaction product obtained by reacting a phenyl metal compound with a substituted silicon compound includes, typically, $(F_{III})F_{VI}SiH(Yj)$ obtained from phenyl metal compounds of the formula (III) and the formula (VI) and a substituted silicon compound (VIII), and $(F_{IV})F_{V}SiH(Yj)$ obtained by reacting phenyl metal compounds of the formula (IV) and the formula (V) with a substituted silicon compound (VIII) (wherein, j represents an integer of 1 to 3, and $F_{III}$ to $F_{VI}$ represent organic residues of phenyl metal compounds of the formulae (III) to (VI)), and the organic silicon compound of the present invention is produced by hydrolyzing and condensing them. In MgX in "M" in the phenyl metal compounds (III) to (VI), X represents a halogen atom.

The halogen atom includes, for example, a chlorine atom, bromine atom and iodine atom.

The above-mentioned phenyl metal compounds (III) to (VI) can be produced by reacting raw material compounds in which "M" in the formulae (III) to (VI) is a hydrogen atom or halogen atom with a reaction reagent such as magnesium, lithium or n-butyllithium and the like, usually in the presence of a reaction solvent.

As the above-mentioned reaction solvent, ether-based reaction solvents (tetrahydrofuran, diethyl ether, t-butyl methyl ether, di-n-butyl ether and the like), and mixtures of the ether-based reaction solvents and hydrocarbon-based reaction solvents (n-hexane, n-heptane and the like), and the like are used.

The phenyl metal compounds (III) to (VI) produced by the above-mentioned reaction can be used in the subsequent reaction in the form of reaction liquid itself, or can be isolated by an ordinary method and used.

$Y_1$ to $Y_3$ in the substituted silicon compound (VII) represent a halogen atom (chlorine atom, bromine atom, iodine atom and the like) or alkoxyl group (methoxy group, ethoxy group, i-propoxy group, n-butoxy group and the like).

The reaction of the phenyl metal compounds (III) to (VI) with the substituted silicon compound (VII) is conducted, usually, in the presence or absence of a reaction solvent in a temperature range of −80 to 200° C.

When the reaction is conducted in the presence of the reaction solvent, ether-based solvents such as tetrahydrofuran, diethyl ether, t-butyl methyl ether, di-n-butyl ether and the like, or mixtures of the ether-based solvents and hydrocarbon-based solvents (n-hexane, n-heptane and the like), and the like are used.

In this reaction, the phenyl metal compounds (III) to (VI) may be added to the substituted silicon compound (VII), or the substituted silicon compound (VII) may be added to the phenyl metal compounds (III) to (VI), and the method of adding the phenyl metal compounds (III) to (VI) to the substituted silicon compound (VII) is more preferable.

Regarding the molar ratio in reacting the phenyl metal compounds (III) to (VI) with the substituted silicon compound (VII), it is preferable that the total mol numbers of the phenyl metal compounds (III) to (VI) is about 1.8 to 2.2 mol per mol of the substituted silicon compound (VII).

In this case, the respective use proportions of the phenyl metal compounds (III) to (VI) may be appropriately adjusted.

The reaction product obtained by reacting the phenyl metal compounds (III) to (VI) with the substituted silicon compound (VII) is hydrolyzed, then, condensed, to obtain an organic silicon compound (I).

The above-mentioned hydrolysis of the reaction product is carried out in the presence of water or an aqueous solution of an inorganic salt (sodium chloride, ammonium chloride and the like).

In the hydrolysis, if necessary, an aqueous solution of an acid such as hydrogen chloride water, sulfuric acid water and the like may be used.

The above-mentioned condensation often progresses simultaneously with hydrolysis, the condensation reaction may be progressed by heating the reaction mixture obtained after hydrolysis up to about 280° C.

Progress of these reactions can be traced by an analysis method such as, for example, gas chromatography, liquid chromatography and the like.

In purifying the organic silicon compound (I), usual means such as distillation, crystallization, column chromatography and the like are used.

As the solvent to be used in crystallization, for example, aromatic hydrocarbon solvents such as toluene, xylene and the like; aliphatic hydrocarbon solvents such as n-hexane, n-heptane and the like; alicyclic hydrocarbon solvents such as cyclohexane and the like; alcohol-based solvents such as methanol, ethanol, i-propanol and the like; ketone-based solvents such as acetone, methyl isobutyl ketone and the like; ester-based solvents such as ethyl acetate and the like; ether-based solvents such as tetrahydrofuran, diethyl ether and the like; nitrile-based solvents such as acetonitrile and the like; amide-based solvents such as dimethylformamide and the like; halogenated hydrocarbon solvents such as chloroform, methylene chloride, chlorobenzene and the like; and mixtures of these solvents, are used.

Thus, the organic silicon compound of the formula (I) is produced.

The organic silicon compound (I) includes, for example, the following compounds.

Organic silicon compounds in which $R_1$ to $R_{20}$ are alkyl groups:

1,1,3,3-tetrakis(2-methylphenyl)disiloxane, 1,1,3,3-tetrakis(3-methylphenyl)disiloxane, 1,1,3,3-tetrakis(4-methylphenyl)disiloxane, 1,1,3,3-tetrakis(2-ethylphenyl)disiloxane, 1,1,3,3-tetrakis(3-ethylphenyl)disiloxane, 1,1,3,3-tetrakis(4-ethylphenyl)disiloxane, 1,1,3,3-tetrakis(2-n-butylphenyl)disiloxane, 1,1,3,3-tetrakis(3-n-butylphenyl)disiloxane, 1,1,3,3-tetrakis(4-n-butylphenyl)disiloxane, 1,1,3,3-tetrakis(2-t-butylphenyl)disiloxane, 1,1,3,3-tetrakis(3-t-butylphenyl)disiloxane, 1,1,3,3-tetrakis(4-t-butylphenyl)disiloxane, 1,1,3,3-tetrakis(2-t-octylphenyl)disiloxane, 1,1,3,3-tetrakis(3-t-octylphenyl)disiloxane, 1,1,3,3-tetrakis(4-t-octylphenyl)disiloxane, 1,1,3,3-tetrakis(2,3-dimethylphenyl)disiloxane, 1,1,3,3-tetrakis(2,4-dimethylphenyl)disiloxane, 1,1,3,3-tetrakis(2,5-dimethylphenyl)disiloxane, 1,1,3,3-tetrakis(2,6-dimethylphenyl)disiloxane, 1,1,3,3-tetrakis(3,4-dimethylphenyl)disiloxane, 1,1,3,3-tetrakis(3,5-dimethylphenyl)disiloxane, 1,1,3,3-tetrakis(2,3-diethylphenyl)disiloxane, 1,1,3,3-tetrakis(2,4-diethylphenyl)disiloxane, 1,1,3,3-tetrakis(2,5-diethylphenyl)disiloxane, 1,1,3,3-tetrakis(2,6-diethylphenyl)disiloxane, 1,1,3,3-tetrakis(3,4-diethylphenyl)disiloxane, 1,1,3,3-tetrakis(3,5-diethylphenyl)disiloxane, 1,1,3,3-tetrakis(2,3-di-n-butylphenyl)disiloxane, 1,1,3,3-tetrakis(2,4-di-n-butylphenyl)disiloxane, 1,1,3,3-tetrakis(2,5-di-n-butylphenyl)disiloxane, 1,1,3,3-tetrakis(2,6-di-n-butylphenyl)disiloxane, 1,1,3,3-tetrakis(3,4-di-n-butylphenyl)disiloxane, 1,1,3,3-tetrakis(3,5-di-n-butylphenyl)disiloxane, 1,1,3,3-tetrakis(2,3-di-t-butylphenyl)disiloxane, 1,1,3,3-tetrakis(2,4-di-t-butylphenyl)disiloxane, 1,1,3,3-tetrakis(2,5-di-t-butylphenyl)disiloxane, 1,1,3,3-tetrakis(2,6-di-t-butylphenyl)disiloxane, 1,1,3,3-tetrakis(3,4-di-t-butylphenyl)disiloxane, 1,1,3,3-tetrakis(3,5-di-t-butylphenyl)disiloxane, 1,1,3,3-tetrakis(2,3-di-t-octylphenyl)disiloxane, 1,1,3,3-tetrakis(2,4-di-t-octylphenyl)disiloxane, 1,1,3,3-tetrakis(2,5-di-t-octylphenyl)disiloxane, 1,1,3,3-tetrakis(2,6-di-t-octylphenyl)disiloxane, 1,1,3,3-tetrakis(3,4-di-t-octylphenyl)disiloxane, 1,1,3,3-tetrakis(3,5-di-t-octylphenyl)disiloxane, 1,1,3,3-tetrakis(2,3,4-trimethylphenyl)disiloxane, 1,1,3,3-tetrakis(2,3,5-trimethylphenyl)disiloxane, 1,1,3,3-tetrakis(2,3,6-trimethylphenyl)disiloxane, 1,1,3,3-tetrakis(2,4,5-trimethylphenyl)disiloxane, 1,1,3,3-tetrakis(2,4,6-trimethylphenyl)disiloxane, 1,1,3,3-tetrakis(2,3,4-triethylphenyl)disiloxane, 1,1,3,3-tetrakis(2,3,5-triethylphenyl)disiloxane, 1,1,3,3-tetrakis(2,3,6-triethylphenyl)disiloxane, 1,1,3,3-tetrakis(2,4,5-triethylphenyl)disiloxane, 1,1,3,3-tetrakis(2,4,6-triethylphenyl)disiloxane, 1,1,3,3-tetrakis(2,3,4-tri-n-butylphenyl)disiloxane, 1,1,3,3-tetrakis(2,3,5-tri-n-butylphenyl)disiloxane, 1,1,3,3-tetrakis(2,3,6-tri-n-butylphenyl)disiloxane, 1,1,3,3-tetrakis(2,4,5-tri-n-butylphenyl)disiloxane, 1,1,3,3-tetrakis(2,4,6-tri-n-butylphenyl)disiloxane, 1,1,3,3-tetrakis(2,3,4-tri-t-butylphenyl)disiloxane, 1,1,3,3-tetrakis(2,3,5-tri-t-butylphenyl)disiloxane, 1,1,3,3-tetrakis(2,3,6-tri-t-butylphenyl)disiloxane, 1,1,3,3-tetrakis(2,4,5-tri-t-butylphenyl)disiloxane, 1,1,3,3-tetrakis(2,4,6-tri-t-butylphenyl)disiloxane, 1,1,3,3-tetrakis(2,3,4-tri-t-octylphenyl)disiloxane, 1,1,3,3-tetrakis(2,3,5-tri-t-octylphenyl)disiloxane, 1,1,3,3-tetrakis(2,3,6-tri-t-octylphenyl)disiloxane, 1,1,3,3-tetrakis(2,4,5-tri-t-octylphenyl)disiloxane, 1,1,3,3-tetrakis(2,4,6-tri-t-octylphenyl)disiloxane.

Organic silicon compounds in which $R_1$ to $R_{20}$ are alkoxyl groups:

1,1,3,3-tetrakis(2-methoxyphenyl)disiloxane, 1,1,3,3-tetrakis(3-methoxyphenyl)disiloxane, 1,1,3,3-tetrakis(4-methoxyphenyl)disiloxane, 1,1,3,3-tetrakis(2-ethoxyphenyl)disiloxane, 1,1,3,3-tetrakis(3-ethoxyphenyl)disiloxane, 1,1,3,3-tetrakis(4-ethoxyphenyl)disiloxane, 1,1,3,3-tetrakis(2-n-butoxyphenyl)disiloxane, 1,1,3,3-tetrakis(3-n-butoxyphenyl)disiloxane, 1,1,3,3-tetrakis(4-n-butoxyphenyl)disiloxane, 1,1,3,3-tetrakis(2-t-butoxyphenyl)disiloxane, 1,1,3,3-tetrakis(3-t-butoxyphenyl)disiloxane, 1,1,3,3-tetrakis(4-t-butoxyphenyl)disiloxane, 1,1,3,3-tetrakis(2-t-octyloxyphenyl)disiloxane, 1,1,3,3-tetrakis(3-t-octyloxyphenyl)disiloxane, 1,1,3,3-tetrakis(4-t-octyloxyphenyl)disiloxane, 1,1,3,3-tetrakis(2,3-dimethoxyphenyl)disiloxane, 1,1,3,3-tetrakis(2,4-dimethoxyphenyl)disiloxane, 1,1,3,3-tetrakis(2,5-dimethoxyphenyl)disiloxane, 1,1,3,3-tetrakis(2,6-dimethoxyphenyl)disiloxane, 1,1,3,3-tetrakis(3,4-dimethoxyphenyl)disiloxane, 1,1,3,3-tetrakis(3,5-dimethoxyphenyl)disiloxane, 1,1,3,3-tetrakis(2,3-diethoxyphenyl)disiloxane, 1,1,3,3-tetrakis(2,4-diethoxyphenyl)disiloxane, 1,1,3,3-tetrakis(2,5-diethoxyphenyl)disiloxane, 1,1,3,3-tetrakis(2,6-diethoxyphenyl)disiloxane, 1,1,3,3-tetrakis(3,4-diethoxyphenyl)disiloxane, 1,1,3,3-tetrakis(3,5-diethoxyphenyl)disiloxane, 1,1,3,3-tetrakis(2,3-di-n-butoxyphenyl)disiloxane, 1,1,3,3-tetrakis(2,4-di-n-butoxyphenyl)disiloxane, 1,1,3,3-tetrakis(2,5-di-n-butoxyphenyl)disiloxane, 1,1,3,3-tetrakis(2,6-di-n-butoxyphenyl)disiloxane, 1,1,3,3-tetrakis(3,4-di-n-butoxyphenyl)disiloxane, 1,1,3,3-tetrakis(3,5-di-n-butoxyphenyl)disiloxane, 1,1,3,3-tetrakis(2,3-di-t-butoxyphenyl)disiloxane, 1,1,3,3-tetrakis(2,4-di-t-butoxyphenyl)disiloxane, 1,1,3,3-tetrakis(2,5-di-t-butoxyphenyl)disiloxane, 1,1,3,3-tetrakis(2,6-di-t-butoxyphenyl)disiloxane, 1,1,3,3-tetrakis(3,4-di-t-butoxyphenyl)disiloxane, 1,1,3,3-tetrakis(3,5-di-t-butoxyphenyl)disiloxane, 1,1,3,3-tetrakis(2,3-di-t-octyloxyphenyl)disiloxane, 1,1,3,3-tetrakis(2,4-di-t-octyloxyphenyl)disiloxane, 1,1,3,3-tetrakis(2,5-di-t-octyloxyphenyl)disiloxane, 1,1,3,3-tetrakis(2,6-di-t-octyloxyphenyl)disiloxane, 1,1,3,3-tetrakis(3,4-di-t-octyloxyphenyl)disiloxane, 1,1,3,3-tetrakis(3,5-di-t-octyloxyphenyl)disiloxane, 1,1,3,3-tetrakis(2,3,4-trimethoxyphenyl)disiloxane, 1,1,3,3-tetrakis(2,3,5-trimethoxyphenyl)disiloxane, 1,1,3,3-tetrakis(2,3,6-trimethoxyphenyl)disiloxane, 1,1,3,3-tetrakis(2,4,5-trimethoxyphenyl)disiloxane, 1,1,3,3-tetrakis(2,4,6-trimethoxyphenyl)disiloxane, 1,1,3,3-tetrakis(2,3,4-triethoxyphenyl)disiloxane, 1,1,3,3-tetrakis(2,3,5-triethoxyphenyl)disiloxane, 1,1,3,3-tetrakis(2,3,6-triethoxyphenyl)disiloxane, 1,1,3,3-tetrakis(2,4,5-triethoxyphenyl)disiloxane, 1,1,3,3-tetrakis(2,4,6-triethoxyphenyl)disiloxane, 1,1,3,3-tetrakis(2,3,4-tri-n-butoxyphenyl)disiloxane, 1,1,3,3-tetrakis(2,3,5-tri-n-butoxyphenyl)disiloxane, 1,1,3,3-tetrakis(2,3,6-tri-n-butoxyphenyl)disiloxane, 1,1,3,3-tetrakis(2,4,5-tri-n-butoxyphenyl)disiloxane, 1,1,3,3-tetrakis(2,4,6-tri-n-butoxyphenyl)disiloxane, 1,1,3,3-tetrakis(2,3,4-tri-t-butoxyphenyl)disiloxane, 1,1,3,3-tetrakis(2,3,5-tri-t-butoxyphenyl)disiloxane, 1,1,3,3-tetrakis(2,3,6-tri-t-butoxyphenyl)disiloxane, 1,1,3,3-tetrakis(2,4,5-tri-t-butoxyphenyl)disiloxane, 1,1,3,3-tetrakis(2,4,6-tri-t-butoxyphenyl)disiloxane, 1,1,3,3-tetrakis(2,3,4-tri-t-octyloxyphenyl)disiloxane, 1,1,3,3-tetrakis(2,3,5-tri-t-octyloxyphenyl)disiloxane, 1,1,3,3-tetrakis(2,3,6-tri-t-octyloxyphenyl)disiloxane, 1,1,3,3-tetrakis(2,4,5-tri-t-octyloxyphenyl)disiloxane, 1,1,3,3-tetrakis(2,4,6-tri-t-octyloxyphenyl)disiloxane.

Organic silicon compounds in which a part of $R_1$ to $R_{20}$ are alkyl groups and remaining groups are alkoxyl groups:

1,1,3,3-tetrakis(2-methyl-3-methoxyphenyl)disiloxane, 1,1,3,3-tetrakis(2-methyl-4-methoxyphenyl)disiloxane, 1,1,3,3-tetrakis(2-methyl-5-methoxyphenyl)disiloxane, 1,1,3,3-tetrakis(2-methyl-6-methoxyphenyl)disiloxane, 1,1,3,3-tetrakis(3-methyl-4-methoxyphenyl)disiloxane, 1,1,3,3-tetrakis(3-methyl-5-methoxyphenyl)disiloxane, 1,1,3,3-tetrakis(2-methoxy-3-methylphenyl)disiloxane, 1,1,3,3-tetrakis(2-methoxy-4-methylphenyl)disiloxane, 1,1,3,3-tetrakis(2-methoxy-5-methylphenyl)disiloxane, 1,1,3,3-tetrakis(3-methoxy-4-methylphenyl)disiloxane, 1,1,3,3-tetrakis(2-methyl-3-ethoxyphenyl)disiloxane, 1,1,3,3-tetrakis(2-methyl-4-ethoxyphenyl)disiloxane, 1,1,3,3-tetrakis(2-methyl-5-ethoxyphenyl)disiloxane, 1,1,3,3-tetrakis(2-methyl-6-ethoxyphenyl)disiloxane, 1,1,3,3-tetrakis(3-methyl-4-ethoxyphenyl)disiloxane, 1,1,3,3-tetrakis(3-methyl-5-ethoxyphenyl)disiloxane, 1,1,3,3-tetrakis(2-ethoxy-3-methylphenyl)disiloxane, 1,1,3,3-tetrakis(2-ethoxy-4-methylphenyl)disiloxane, 1,1,3,3-tetrakis(2-ethoxy-5-methylphenyl)disiloxane, 1,1,3,3-tetrakis(3-ethoxy-4-methylphenyl)disiloxane, 1,1,3,3-tetrakis(2-methyl-3-n-butoxyphenyl)disiloxane, 1,1,3,3-tetrakis(2-methyl-4-n-butoxyphenyl)disiloxane, 1,1,3,3-tetrakis(2-methyl-5-n-butoxyphenyl)disiloxane, 1,1,3,3-tetrakis(2-methyl-6-n-butoxyphenyl)disiloxane, 1,1,3,3-tetrakis(3-methyl-4-n-butoxyphenyl)disiloxane, 1,1,3,3-tetrakis(3-methyl-5-n-butoxyphenyl)disiloxane, 1,1,3,3-tetrakis(2-n-butoxy-3-methylphenyl)disiloxane, 1,1,3,3-tetrakis(2-n-butoxy-4-methylphenyl)disiloxane, 1,1,3,3-tetrakis(2-n-butoxy-5-methylphenyl)disiloxane, 1,1,3,3-tetrakis(3-n-butoxy-4-methylphenyl)disiloxane, 1,1,3,3-tetrakis(2-ethyl-3-methoxyphenyl)disiloxane, 1,1,3,3-tetrakis(2-ethyl-4-methoxyphenyl)disiloxane, 1,1,3,3-tetrakis(2-ethyl-5-methoxyphenyl)disiloxane, 1,1,3,3-tetrakis(2-ethyl-6-methoxyphenyl)disiloxane, 1,1,3,3-tetrakis(3-ethyl-4-methoxyphenyl)disiloxane, 1,1,3,3-tetrakis(3-ethyl-5-methoxyphenyl)disiloxane, 1,1,3,3-tetrakis(2-methoxy-3-ethylphenyl)disiloxane, 1,1,3,3-tetrakis(2-methoxy-4-ethylphenyl)disiloxane, 1,1,3,3-tetrakis(2-methoxy-5-ethylphenyl)disiloxane, 1,1,3,3-tetrakis(3-methoxy-4-ethylphenyl)disiloxane, 1,1,3,3-tetrakis(2-ethyl-3-ethoxyphenyl)disiloxane, 1,1,3,3-tetrakis(2-ethyl-4-ethoxyphenyl)disiloxane, 1,1,3,3-tetrakis(2-ethyl-5-ethoxyphenyl)disiloxane, 1,1,3,3-tetrakis(2-ethyl-6-ethoxyphenyl)disiloxane, 1,1,3,3-tetrakis(3-ethyl-4-ethoxyphenyl)disiloxane, 1,1,3,3-tetrakis(3-ethyl-5-ethoxyphenyl)disiloxane, 1,1,3,3-tetrakis(2-ethoxy-3-ethylphenyl)disiloxane, 1,1,3,3-tetrakis(2-ethoxy-4-ethylphenyl)disiloxane, 1,1,3,3-tetrakis(2-ethoxy-5-ethylphenyl)disiloxane, 1,1,3,3-tetrakis(3-ethoxy-4-ethylphenyl)disiloxane, 1,1,3,3-tetrakis(2-ethyl-3-n-butoxyphenyl)disiloxane, 1,1,3,3-tetrakis(2-ethyl-4-n-butoxyphenyl)disiloxane, 1,1,3,3-tetrakis(2-ethyl-5-n-butoxyphenyl)disiloxane, 1,1,3,3-tetrakis(2-ethyl-6-n-butoxyphenyl)disiloxane, 1,1,3,3-tetrakis(3-ethyl-4-n-butoxyphenyl)disiloxane, 1,1,3,3-tetrakis(3-ethyl-5-n-butoxyphenyl)disiloxane, 1,1,3,3-tetrakis(2-n-butoxy-3-ethylphenyl)disiloxane, 1,1,3,3-tetrakis(2-n-butoxy-4-ethylphenyl)disiloxane, 1,1,3,3-tetrakis(2-n-butoxy-5-ethylphenyl)disiloxane, 1,1,3,3-tetrakis(3-n-butoxy-4-ethylphenyl)disiloxane, 1,1,3,3-tetrakis(2-t-butyl-3-methoxyphenyl)disiloxane, 1,1,3,3-tetrakis(2-t-butyl-4-methoxyphenyl)disiloxane, 1,1,3,3-tetrakis(2-t-butyl-5-methoxyphenyl)disiloxane, 1,1,3,3-tetrakis(2-t-butyl-6-methoxyphenyl)disiloxane, 1,1,3,3-tetrakis(3-t-butyl-4-methoxyphenyl)disiloxane, 1,1,3,3-tetrakis(3-t-butyl-5-methoxyphenyl)disiloxane, 1,1,3,3-tetrakis(2-methoxy-3-t-butylphenyl)disiloxane, 1,1,3,3-tetrakis(2-methoxy-4-t-butylphenyl)disiloxane, 1,1,3,3-tetrakis(2-methoxy-5-t-butylphenyl)disiloxane, 1,1,3,3-tetrakis(3-methoxy-4-t-butylphenyl)disiloxane, 1,1,3,3-tetrakis(2-t-butyl-3-ethoxyphenyl)disiloxane, 1,1,3,3-tetrakis(2-t-butyl-4-ethoxyphenyl)disiloxane, 1,1,3,3-tetrakis(2-t-butyl-5-ethoxyphenyl)disiloxane, 1,1,3,3-tetrakis(2-t-butyl-6-ethoxyphenyl)disiloxane, 1,1,3,3-tetrakis(3-t-butyl-4-ethoxyphenyl)disiloxane, 1,1,3,3-tetrakis(3-t-butyl-5-ethoxyphenyl)disiloxane, 1,1,3,3-tetrakis(2-ethoxy-3-t-butylphenyl)disiloxane, 1,1,3,3-tetrakis(2-ethoxy-4-t-butylphenyl)disiloxane, 1,1,3,3-tetrakis(2-ethoxy-5-t-butylphenyl)disiloxane, 1,1,3,3-tetrakis(3-ethoxy-4-t-butylphenyl)disiloxane, 1,1,3,3-tetrakis(2-t-butyl-3-n-butoxyphenyl)disiloxane, 1,1,3,3-tetrakis(2-t-butyl-4-n-butoxyphenyl)disiloxane, 1,1,3,3-tetrakis(2-t-butyl-5-n-butoxyphenyl)disiloxane, 1,1,3,3-tetrakis(2-t-butyl-6-n-butoxyphenyl)disiloxane, 1,1,3,3-tetrakis(3-t-butyl-4-n-butoxyphenyl)disiloxane, 1,1,3,3-tetrakis(3-t-butyl-5-n-butoxyphenyl)disiloxane, 1,1,3,3-tetrakis(2-n-butoxy-3-t-butylphenyl)disiloxane, 1,1,3,3-tetrakis(2-n-butoxy-4-t-butylphenyl)disiloxane, 1,1,3,3-tetrakis(2-n-butoxy-5-t-butylphenyl)disiloxane, 1,1,3,3-tetrakis(3-n-butoxy-4-t-butylphenyl)disiloxane.

Organic silicon compounds in which $R_1$ to $R_{20}$ represent an alkoxyalkyl group, aryloxy group, cycloalkyl group, alkylcycloalkyl group or aryl group:

1,1,3,3-tetrakis(2-methoxymethylphenyl)disiloxane, 1,1,3,3-tetrakis(3-methoxymethylphenyl)disiloxane, 1,1,3,3-tetrakis(4-methoxymethylphenyl)disiloxane, 1,1,3,3-tetrakis(2-phenyloxyphenyl)disiloxane, 1,1,3,3-tetrakis(3-phenyloxyphenyl)disiloxane, 1,1,3,3-tetrakis(4-phenyloxyphenyl)disiloxane, 1,1,3,3-tetrakis(2-cyclohexylphenyl)disiloxane, 1,1,3,3-tetrakis(3-cyclohexylphenyl)disiloxane, 1,1,3,3-tetrakis(4-cyclohexylphenyl)disiloxane, 1,1,3,3-tetrakis(2-biphenyl)disiloxane, 1,1,3,3-tetrakis(3-biphenyl)disiloxane, 1,1,3,3-tetrakis(4-biphenyl)disiloxane.

Organic silicon compounds in which $R_1$ to $R_{20}$ represent an alkylthio group or dialkylamino group:

1,1,3,3-tetrakis(2-methylthiophenyl)disiloxane, 1,1,3,3-tetrakis(3-methylthiophenyl)disiloxane, 1,1,3,3-tetrakis(4-methylthiophenyl)disiloxane, 1,1,3,3-tetrakis(2-N,N-dimethylaminophenyl)disiloxane, 1,1,3,3-tetrakis(3-N,N-dimethylaminophenyl)disiloxane, 1,1,3,3-tetrakis(4-N,N-dimethylaminophenyl)disiloxane, 1,1,3,3-tetrakis(2-N,N-diethylaminophenyl)disiloxane, 1,1,3,3-tetrakis(3-N,N-diethylaminophenyl)disiloxane, 1,1,3,3-tetrakis(4-N,N-diethylaminophenyl)disiloxane, 1,1,3,3-tetrakis(2-N,N-di-n-butylaminophenyl)disiloxane, 1,1,3,3-tetrakis(3-N,N-di-n-butylaminophenyl)disiloxane, 1,1,3,3-tetrakis(4-N,N-di-n-butylaminophenyl)disiloxane.

Asymmetric organic silicon compounds:

1,3-diphenyl-1,3-bis(2-methylphenyl)disiloxane, 1,3-diphenyl-1,3-bis(3-methylphenyl)disiloxane, 1,3-diphenyl-1,3-bis(4-methylphenyl)disiloxane, 1,3-diphenyl-1,3-bis(2-t-butylphenyl)disiloxane, 1,3-diphenyl-1,3-bis(3-t-butylphenyl)disiloxane, 1,3-diphenyl-1,3-bis(4-t-butylphenyl)disiloxane, 1,3-diphenyl-1,3-bis(2-methoxyphenyl)disiloxane, 1,3-diphenyl-1,3-bis(3-methoxyphenyl)disiloxane, 1,3-diphenyl-1,3-bis(4-methoxyphenyl)disiloxane, 1,3-diphenyl-1,3-bis(2,3-dimethoxyphenyl)disiloxane, 1,3-diphenyl-1,3-bis(2,4-dimethoxyphenyl)disiloxane, 1,3-diphenyl-1,3-bis(2,5-dimethoxyphenyl)disiloxane, 1,3-diphenyl-1,3-bis(2,6-dimethoxyphenyl)disiloxane, 1,3-diphenyl-1,3-bis(3,4-dimethoxyphenyl)disiloxane, 1,3-diphenyl-1,3-bis(3,5-dimethoxyphenyl)disiloxane, 1,3-diphenyl-1,3-bis(2-methyl-3-methoxyphenyl)disiloxane, 1,3-diphenyl-1,3-bis(2-methyl-4-methoxyphenyl)disiloxane, 1,3-diphenyl-1,3-bis(2-methyl-5-methoxyphenyl)disiloxane, 1,3-diphenyl-1,3-bis(2-methyl-6-methoxyphenyl)disiloxane, 1,3-diphenyl-1,3-bis(3-methyl-4-methoxyphenyl)disiloxane, 1,3-diphenyl-1,3-bis(3-methyl-5-methoxyphenyl)disiloxane, 1,3-diphenyl-1,3-bis(2-methoxy-3-methylphenyl)disiloxane, 1,3-diphenyl-1,3-bis(2-methoxy-4-methylphenyl)disiloxane, 1,3-diphenyl-1,3-bis(2-methoxy-5-methylphenyl)disiloxane, 1,3-diphenyl-1,3-bis(3-methoxy-4-methylphenyl)disiloxane, and the like.

Among the organic silicon compounds of the formula (I) of the present invention, preferable are compounds wherein $R_1$ to $R_{20}$ in the formula (I) represent each independently a hydrogen atom, alkyl group having 1 to 30 carbon atoms, alkoxyl group having 1 to 30 carbon atoms, alkoxyalkyl group having 2 to 30 carbon atoms, aryloxy group having 6 to 18 carbon atoms, aryl group having 6 to 18 carbon atoms, cycloalkyl group having 5 to 8 carbon atoms, alkylcycloalkyl group having 6 to 20 carbon atoms, alkylthio group having 1 to 30 carbon atoms or dialkylamino group having 2 to 30 carbon atoms, $R_1$ to $R_{20}$ in the formula (I) do not all represent a hydrogen atom simultaneously, and 1 to 3 hydrogen atoms in the aryloxy group having 6 to 18 carbon atoms and the aryl group having 6 to 18 carbon atoms may be substituted by 1 to 3 substituents selected from the group consisting of alkyl groups having 1 to 30 carbon atoms, alkoxyl groups having 1 to 30 carbon atoms and alkoxyalkyl groups having 2 to 30 carbon atoms.

Among the above-mentioned organic silicon compounds, more preferable are compounds wherein $R_1$ to $R_{20}$ in the formula (I) represent each independently a hydrogen atom, alkyl group having 1 to 30 carbon atoms or alkoxyl group having 1 to 30 carbon atoms, and $R_1$ to $R_{20}$ in the formula (I) do not all represent a hydrogen atom simultaneously.

Further, among the organic silicon compounds of the present invention, particularly preferable are compounds wherein $R_1$ to $R_{20}$ in the formula (I) represent each independently a hydrogen atom, alkyl group having 1 to 30 carbon atoms or alkoxyl group having 1 to 30 carbon atoms, and $R_1$, $R_6$, $R_{11}$ and $R_{16}$ are identical, $R_2$, $R_7$, $R_{12}$ and $R_{17}$ are identical, $R_3$, $R_8$, $R_{13}$ and $R_{18}$ are identical, $R_4$, $R_9$, $R_{14}$ and $R_{19}$ are identical and $R_5$, $R_{10}$, $R_{15}$ and $R_{20}$ are identical, and $R_1$ to $R_{20}$ in the formula (I) do not all represent a hydrogen atom simultaneously.

Of the method of producing an organic silicon compound of the formula (I) of the present invention, preferable is a method of producing a compound wherein $R_1$ to $R_{20}$ in the formula (I) represent each independently a hydrogen atom, alkyl group having 1 to 30 carbon atoms, alkoxyl group having 1 to 30 carbon atoms, alkoxyalkyl group having 2 to 30 carbon atoms, aryloxy group having 6 to 18 carbon atoms, aryl group having 6 to 18 carbon atoms, cycloalkyl group having 5 to 8 carbon atoms, alkylcycloalkyl group having 6 to 20 carbon atoms, alkylthio group having 1 to 30 carbon atoms or dialkylamino group having 2 to 30 carbon atoms, $R_1$ to $R_{20}$ in the formula (I) do not all represent a hydrogen atom simultaneously, and 1 to 3 hydrogen atoms in the aryloxy group having 6 to 18 carbon atoms and the aryl group having 6 to 18 carbon atoms may be substituted by 1 to 3 substituents selected from the group consisting of alkyl groups having 1 to 30 carbon atoms, alkoxyl groups having 1 to 30 carbon atoms and alkoxyalkyl groups having 2 to 30 carbon atoms.

Of the method of producing a compound, more preferable is a method of producing a compound wherein $R_1$ to $R_{20}$ in the formula (I) represent each independently a hydrogen atom, alkyl group having 1 to 30 carbon atoms or alkoxyl group having 1 to 30 carbon atoms, and $R_1$ to $R_{20}$ in the formula (I) do not all represent a hydrogen atom simultaneously.

Further, of the method of producing an organic silicon compound of the present invention, particularly preferable is a method of producing a compound wherein $R_1$ to $R_{20}$ in the formula (I) represent each independently a hydrogen atom, alkyl group having 1 to 30 carbon atoms or alkoxyl group having 1 to 30 carbon atoms, and $R_1$, $R_6$, $R_{11}$ and $R_{16}$ are identical, $R_2$, $R_7$, $R_{12}$ and $R_{17}$ are identical, $R_3$, $R_8$, $R_{13}$ and $R_{18}$ are identical, $R_4$, $R_9$, $R_{14}$ and $R_{19}$ are identical and $R_5$, $R_{10}$, $R_{15}$ and $R_{20}$ are identical, $R_1$ to $R_{20}$ in the formula (I) do not all represent a hydrogen atom simultaneously.).

The organic silicon compound (I) of the present invention is useful as a stabilizer for thermal degradation, oxidation degradation and the like of an organic material. The above-mentioned organic material includes, for example, the following materials. These organic materials are used singly or as a mixture of two or more materials.

Thermoplastic resins described below:

(1) polyethylene such as high density polyethylene (HD-PE), low density polyethylene (LD-PE), linear low density polyethylene (LLD-PE), and the like, (2) polypropylene, (3) ethylene/propylene copolymer, (4) methylpentene polymer, (5) EEA (ethylene/ethyl acrylate copolymer) resin, (6) ethylene/vinyl acetate copolymer resin, (7) polystyrenes such as polystyrene, poly(p-methylstyrene), poly(a-methylstyrene) and the like, (8) AS (acrylonitrile/styrene copolymer) resin, (9) ABS (acrylonitrile/butadiene/styrene copolymer) resin such as transparent ABS resin and the like, (10) AAS (special acryl rubber/acrylonitrile/styrene copolymer) resin, (11) ACS (acrylonitrile/chlorinated polyethylene/styrene copolymer) resin, (12) AB (acrylonitrile/butadienecopolymer) resin, (13) MS (methyl methacrylate/styrene copolymer) resin, (14) chlorinatedpolyethylene, polychloroprene, chlorinated rubber, (15) polyvinyl chloride and polyvinylidene chloride, (16) methacryl resin, (17) ethylene/vinyl alcohol copolymer resin, (18) polyacrylate, (19) ionomer resin, (20) polyvinyl alcohol, (21) cellulose-based resin such as cellulose triacetate and the like, (22) polyurethane, the following engineering resins (23) to (34);

resins (35) to (40), and cyclic polyolefin resin (41) denoted by a registered trade mark described below.

(23) fluorine resin such as polytetrafluoroethylene and the like, (24) modified polyphenylene ether resin and polyphenylene sulfide resin, (25) polyacetal, (26) polyamide, (27) polyester resin such as polyethylene terephthalate, polybutylene terephthalate, liquid crystal polymer (LCP), polylactic acid and the like, (28) polycarbonate, (29) polysulfone, polyether ether ketone, and polyether sulfone, (30) aromatic polyester resin, (31) polyamideimide, (32) polyimide, (33) polyallylate and (34) polyether imide;

(35) polybutadiene, (36) 1,2-polybutadiene, (37) polyisoprene, (38) block copolymer and hydrogenated styrene/butadiene copolymer, (39) block copolymer and hydrogenated styrene/isoprene copolymer, (40) butadiene/acrylonitrile copolymer;

(41) cyclic polyolefin resin;

Topas (registered trademark of Ticona):

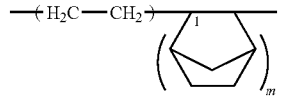

(in the formula, l and m represent a positive integer)

ARTON (registered trademark of JSR):

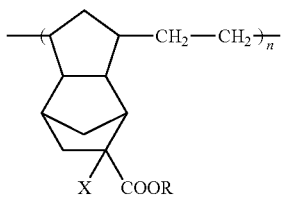

(in the formula, n represents a positive integer. X and R represent a substituent such as an alkyl group and the like)

APEL (registered trademark of Mitsui Chemical Co., Ltd.):

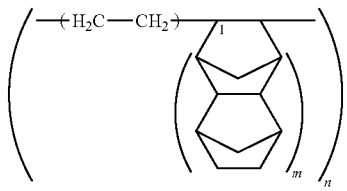

(in the formula, l, m and n represent each independently a positive integer)

ZEONEX (registered trademark of Nippon Zeon):

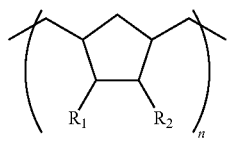

(in the formula, n represents a positive integer. $R_1$ and $R_2$ in the formula represent each independently a substituent such as an alkyl group and the like)

(42) silicone rubber, (43) epichlorohydrin rubber, (44) acryl rubber, (45) natural rubber, (46) chlorine rubber-based paint, (47) polyester resin paint, (48) urethane resin paint, (49) epoxy resin paint, (50) acryl resin paint, (51) vinyl resin paint, (52) aminoalkyd resin paint, (53) alkyd resin paint, (54) nitrocellulose resin paint, (55) oily paint, (56) wax, and the like.

Thermosetting resins (57) to (64) described below:

(57) epoxy resin, (58) diallylphthalate prepolymer, (59) silicone resin, (60) unsaturated polyester resin, (61) acryl-modified benzoquanamine resin, (62) benzoguanamine/melamine resin, (63) urea resin and (64) phenol resin.

Of the organic material composition of the present invention, preferable are compositions containing a thermoplastic resin ((1) to (41) described above) as an organic material.

Among these compositions containing a thermoplastic resin, compositions containing a polyolefin such as polyethylene, polypropylene, cyclic polyolefin resin (41) and the like; compositions containing an engineering resin ((23) to (34)) such as polyamide, polyethylene terephthalate, polybutylene terephthalate and the like are more preferable.

Among the organic material compositions containing an engineering resin, more preferable are compositions containing an engineering resin having an ester bond.

Among these compositions containing an engineering resin having an ester bond, compositions containing a polycarbonate or polyester are particularly preferable, and compositions containing a polycarbonate are particularly preferable. Further, among the above-mentioned organic material compositions containing a polyolefin such as polyethylene, polypropylene, cyclic polyolefin resin and the like, more preferable are compositions containing polypropylene or cyclic polyolefin resin.

The polyolefins described above are not particularly restricted.

For example, polyolefins obtained by radical polymerization may be used, and polyolefins produced by polymerization using a catalyst containing a metal of IVb, Vb, VIb or VIII group in the periodic table may also be used. As the above-mentioned catalyst containing a metal, metal complexes having an oxide, halide, alcoholate, ester, aryl or the like coordinated by one or more ligands, for example, by p or d bond may be permissible, and these complexes may be used as the are, or may be carried on a base material such as magnesium chloride, titanium chloride, alumina, silicon oxide and the like.

As the above-mentioned polyolefin, those produced using, for example, Ziegler Natta catalyst, TNZ catalyst, metallocene catalyst, Phillips catalyst and the like are preferably used.

Of engineering resins, the polyamide resin may advantageously be a resin having an amide bond in a polymer chain and which can be melted by heating.

For example, those produced by any method of a condensation reaction of diamines with dicarboxylic acids, a condensation reaction of aminocarboxylic acids, ring-opening of lactams, and the like may also be permissible.

Specific examples of these polyamide resins include nylon 66, nylon 69, nylon 610, nylon 612, poly-vis(p-aminocyclohexyl)methanedodecamide, nylon 46, nylon 6, nylon 12, nylon 66/6 as a copolymer of nylon 66 and nylon 6, and copolymers such as nylon 6/12.

Of engineering resins, the polyester resin may advantageously be a resin having an ester bond in a polymer chain and which can be melted by heating. Examples thereof include polyesters such as polyethylene terephthalate, polybutylene terephthalate and the like obtained by polycondensation of dicarboxylic acids with dihydroxy compounds, and the like. The polyester may be a homo-polyester or co-polyester.

As the polycarbonate to be used in the present invention, mentioned are, for example, resins produced by reacting a divalent phenol with a carbonate precursor such as carbonyl halide, haloformate, carbonate ester and the like.

Examples of the above-mentioned divalent phenol include bisphenol A, hydroquinone, methylhydroquinone, resorcinol, 2,2-bis(4-hydroxyphenyl)pentane, biphenol, bis(2-hydroxyphenyl)methane, bis(4-hydroxyphenyl)methane, 1,1-bis(4-hydroxyphenyl)ethane, 3,3-bis(4-hydroxyphenyl)pentane, 2,2'-dihydroxybiphenyl, 1,5-dihydroxynaphthalene, 2,6-dihydroxynaphthalene, bis(4-hydroxyphenyl)sulfone, bis(3,5-dimethyl-4-hydroxyphenyl)sulfone, 2,2-bis(3,5-dimethyl-4-hydroxyphenyl)propane, 2,4'-dihydroxydiphenylsulfone, 4,4'-dihydroxydiphenyl ether, 4,4'-dihydroxy-2,5-dimethylphenyl ether, 2,2-bis(3,5-dichloro-4-hydroxyphenyl)propane, 2,2-bis(3,5-dibromo-4-hydroxyphenyl)propane, 2,2-bis(3-chloro-4-hydroxyphenyl)propane, 2,2-bis(3-bromo-4-hydroxyphenyl)propane, 2,2-bis(3-fluoro-4-hydroxyphenyl)propane, 2,2-bis(4-hydroxyphenyl)-1,1,1,3,3,3-hexafluoropropane, 1,1-bis(4-hydroxyphenyl)cyclohexane, 1,1-bis(3,5-dichloro-4-hydroxyphenyl)cyclohexane, 4,4'-dihydroxybenzophenone, 3,3',5,5'-tetramethyl-4,4'-dihydroxybenzophenone, bis(4-hydroxyphenyl)sulfide, bis(3-methyl-4-hydroxyphenyl)sulfide, bis(3,5-dimethyl-4-hydroxyphenyl)sulfide, bis(4-hydroxyphenyl)sulfide, 9,9-bis(4-hydroxyphenyl) fluorene and the like.

As the above-mentioned carbonyl halide, for example, phosgene, carbonyl bromide and the like are mentioned.

As the above-mentioned haloformate, for example, haloformates of divalent phenol such as hydroquinone bischloroformate and the like, glycol formates such as ethylene glycol haloformate and the like, and the like are mentioned.

As the above-mentioned carbonate ester, for example, diphenyl carbonate, di(chlorophenyl)carbonate, di(tolyl)carbonate, dinaphthyl carbonate, dimethyl carbonate and the like are mentioned.

As the polycarbonate to be used in the present invention, branched polycarbonates are also mentioned.

The branched polycarbonate can be prepared by reacting the above-mentioned carbonate precursor with a phenol mixture of divalent phenol and a compound having three or more phenolic hydroxyl groups.

Example of the compound having three or more phenolic hydroxyl groups include 1,3,5-trihydroxybenzene, 2,4-bis(4-hydroxyphenylisopropyl)phenol, 2,6-bis(2-hydroxy-5-methylbenzyl)-4-methylphenol, 2-(4-hydroxyphenyl)-2-(2,4-dihydroxyphenyl)propane, 1,4-bis{di(4-hydroxyphenyl)methyl}benzene and the like. The above-mentioned polycarbonate can be produced by an interfacial polymerization method, pyridine method, transesterification method and the like. The polycarbonate produced by this method may be a homopolymer or copolymer. The polycarbonate may be a polyester carbonate or polyphosphonate carbonate.

The molecular weight of the polycarbonate is in a range of preferably 10000 to 100000, more preferably 12000 to 50000, in terms of the viscosity-average molecular weight (value reduced by methylene chloride melt viscosity at 25° C.).

The polymer carbonate may also be a polymer alloy. As resins other than the polycarbonate to form the polymer alloy, Polyolefins such as polyethylene, polypropylene and the like;

Methacrylic resins such as polymethyl methacrylate and the like;
Acrylonitrilebutadienestyrene (ABS resin);
Saturated polyester (PET, PBT);
Polyamide;
Polyphenylene ether (PPE);
Polyester-based resin;
Acrylate-based resin;
Silicone-based resin;
Polyimide resin;
Polyether imide resin;
Polyurethane;
Polyphenylene sulfide resin;
Polysulfone resin;
Polystyrene resin;
Acrylonitrile-styrene copolymer (AS);
Phenol resin;
Epoxy resin;
Styrene/butadiene/styrene block copolymer (SBS);
Isobutylene/isoprene rubber;
Styrene/butadiene rubber;
Ethylene/propylene rubber;
Acrylic elastomer;
Polyester-based elastomer;
Polyamide-based elastomer;
Methyl methacrylate/butadiene/styrene (MBS);
Methyl methacrylate/acrylonitrile/styrene (MAS) thermoplastic elastomer;
Hydrogenated styrene/butadiene/styrene block copolymer (SEBS);
Styrene/isoprene/styrene block copolymer (SIS);
Hydrogenated styrene/isoprene/styrene block copolymer (SEPS) and the like mentioned.

Further, the polycarbonate may be that which is filled with glass fiber, carbon fiber, fluorine resin and the like.

The organic material composition of the present invention is characterized in that it contains the above-mentioned organic material and the above-mentioned organic silicon compound (I) and the weight ratio of the organic material to the organic silicon compound is 100:0.0001 to 100:10.

In the organic material composition of the present invention, when the weight ratio of the organic material to the organic silicon compound (I) is smaller than 100:0.0001, degradation of the organic material cannot be prevented sufficiently in some cases.

On the other hand, even if the weight ratio of the organic material to the organic silicon compound (I) is over 100:10, the effect of preventing degradation of the organic material is not improved so much, leading to economical disadvantage.

As the organic material composition of the present invention, preferable are compositions (wherein $R_1$ to $R_{20}$ in the formula (I) represent each independently a hydrogen atom, alkyl group having 1 to 30 carbon atoms, alkoxyl group having 1 to 30 carbon atoms, alkoxyalkyl group having 2 to 30 carbon atoms, aryloxy group having 6 to 18 carbon atoms, aryl group having 6 to 18 carbon atoms, cycloalkyl group having 5 to 8 carbon atoms, alkylcycloalkyl group having 6 to 20 carbon atoms, alkylthio group having 1 to 30 carbon atoms or dialkylamino group having 2 to 30 carbon atoms, $R_1$ to $R_{20}$ in the formula (I) do not all represent a hydrogen atom simultaneously, and 1 to 3 hydrogen atoms in the aryloxy group having 6 to 18 carbon atoms and the aryl group having 6 to 18 carbon atoms may be substituted by 1 to 3 substituents selected from the group consisting of alkyl groups having 1 to 30 carbon atoms, alkoxyl groups having 1 to 30 carbon atoms and alkoxyalkyl groups having 2 to 30 carbon atoms.

As the organic material composition of the present invention, more preferable are compositions (wherein, $R_1$ to $R_{20}$ in the formula (I) represent each independently a hydrogen atom, alkyl group having 1 to 30 carbon atoms or alkoxyl group having 1 to 30 carbon atoms, and $R_1$ to $R_{20}$ in the formula (I) do not all represent a hydrogen atom simultaneously.

As the organic material composition of the present invention, particularly preferable are compositions (wherein, $R_1$ to $R_{20}$ in the formula (I) represent each independently a hydrogen atom, alkyl group having 1 to 30 carbon atoms or alkoxyl group having 1 to 30 carbon atoms, and $R_1$, $R_6$, $R_{11}$ and $R_{16}$ are identical, $R_2$, $R_7$, $R_{12}$ and $R_{17}$ are identical, $R_3$, $R_8$, $R_{13}$ and $R_{18}$ are identical, $R_4$, $R_9$, $R_{14}$ and $R_{19}$ are identical and $R_5$, $R_{10}$, $R_{15}$ and $R_{20}$ are identical. Here, $R_1$ to $R_{20}$ in the formula (I) do not all represent a hydrogen atom simultaneously.).

The organic material composition of the present invention may contain, if necessary, further other additives, for example, a phenol-based antioxidant, phosphorus-based antioxidant, sulfur-based antioxidant, ultraviolet absorber, photo-stabilizer, hydroxylamine, metal inactivating agent, metal soaps, nucleating agent, lubricant, de-fogging agent, plasticizer, flame retardant, releasing agent, anti-static agent, pigment, dye, filler, foaming agent, organic peroxide and the like.

Further, benzofuranones, indolines and the like described in U.S. Pat. Nos. 4,325,853, 4,338,244, 5,175,312, 5,216,053 and 5,252,643, DE-A-4,316,611, DE-A-4,316,622, DE-A-4,316,876, EP-A-589,839, EP-A-591-102, CA-2,132,132 and the like can also be added.

Furthermore, epoxy compounds such as epoxidated soybean oil and the like, and oxetane-based compounds can also be added.

When the organic material in the organic material composition of the present invention is a polycarbonate, additives which can be added other than organic silicon compounds include phenol-based antioxidants, phosphorus-based antioxidants, sulfur-based antioxidants, ultraviolet absorbers, releasing agents, dyes, flame retardants, anti-static agents, pigments, fillers and the like.

As the organic material in the organic material composition of the present invention, the above-mentioned thermoplastic resins are preferable.

As the thermoplastic resin, the above-mentioned polyolefins or engineering resins are preferable. As the engineering resin, the above-mentioned polycarbonates or the above-mentioned polyesters are preferable.

As the above-mentioned engineering resin, polycarbonates are particularly preferable.

Further, as the above-mentioned polyolefin, polypropylene or cyclic polyolefins are preferable.

When the organic material in the organic material composition of the present invention is a polycarbonate, the above-mentioned phenol-based antioxidant includes the following antioxidants (1) to (17).

(1) Alkylated Monophenol 2,6-di-t-butyl-4-methylphenol, 2,4,6-tri-t-butylphenol, 2,6-di-t-butylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(a-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6-(1'-methylheptadecyl-1'-yl)phenol or 2,4-dimethyl-6-(1'-methyltridecyl-1'-yl)phenol, and mixtures thereof.

(2) Alkylthiomethylphenol 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol, and mixtures thereof.

(3) Hydroquinone and Alkylated Hydroquinone 2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-di-t-butyl-4-hydroxyphenyl)adipate, and mixtures thereof.

(4) Tocopherol a-tocopherol, β-tocopherol, γ-tocopherol, d-tocopherol, and mixtures thereof.

(5) Hydroxylated Thiodiphenyl Ether 2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenyl)disulfide, and mixtures thereof.

(6) Alkylidenebisphenol and Derivatives Thereof 2,2'-methylenebis(4-methyl-6-t-butylphenol), 2,2'-methylenebis(4-ethyl-6-t-butylphenol), 2,2'-methylenebis[4-methyl-6-(a-methylcyclohexyl)phenol], 2,2'-methylenebis(4-methyl-6-cyclohexylphenol), 2,2'-methylenebis(4-methyl-6-nonylphenol), 2,2'-methylenebis(4,6-di-t-butylphenol), 2,2'-ethylidenebis(4,6-di-t-butylphenol), 2,2'-ethylidenebis(4-isobutyl-6-t-butylphenol), 2,2'-methylenebis[6-(a-methylbenzyl)-4-nonylphenol], 2,2'-methylenebis[6-(a,a-dimethylbenzyl)-4-nonylphenol], 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 2,6-bis(3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, ethylene glycol bis[3,3-bis-3'-t-butyl-4'-hydroxyphenyl)butylate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, and mixtures thereof.

(7) O-, N- and S-benzyl Derivatives 3,5,3',5'-tetra-t-butyl-4,4'-dihydroxydibenzyl ether, octadecyl-4-hydroxy-3,5-dimethylbenzyl mercaptoacetate, tris(3,5-di-t-butyl-4-hydroxybenzyl)amine, bis(4-t-butyl-3-hydroxy-2,6-dimethylbenzyl)dithioterephthalate, bis(3,5-di-t-butyl-4-hydroxybenzyl)sulfide, isooctyl-3,5-di-t-butyl-4-hydroxybenzyl mercaptoacetate, and mixtures thereof.

(8) Hydroxybenzylated Malonate Derivatives dioctadecyl-2,2-bis(3,5-di-t-butyl-2-hydroxybenzyl)malonate, dioctadecyl-2-(3-t-butyl-4-hydroxy-5-methylbenzyl)malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate, and mixtures thereof.

(9) Aromatic Hydroxybenzyl Derivatives 1,3,5-trimethyl-2,4,6-tris(3,5-di-t-butyl-4-hydroxybenzyl)benzene, 1,4-bis(3,5-di-t-butyl-4-hydroxybenzyl)-2,3,5,6-tetramethyl benzene, 2,4,6-tris(3,5-t-butyl-4-hydroxybenzyl)phenol, and mixtures thereof.

(10) Triazine Derivatives 2,4-bis(n-octylthio)-6-(4-hydroxy-3,5-di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-phenoxy)-1,3,5-triazine, tris(4-t-butyl-3-hydroxy-2,6-dimethylbenzyl)isocyanurate, tris(3,5-di-t-butyl-4-hydroxybenzyl)isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'-di-t-butyl-4'-hydroxycinnamoyloxy)ethyl]isocyanurate, and mixtures thereof.

(11) Benzyl Phosphonate Derivatives dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonate monoester, and mixtures thereof.

(12) Acylaminophenol Derivatives 4-hydroxylaurylic anilide, 4-hydroxystearic anilide, octyl-N-(3,5-di-t-butyl-4-hydroxyphenyl)carbonate, and mixtures thereof.

(13) Esters of β-(3,5-di-t-butyl-4-hydroxyphenyl)propionic acid and the following mono-hydric or poly-hydric alcohol methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane, and mixtures thereof.

(14) Esters of β-(5-t-butyl-4-hydroxy-3-methylphenyl)propionic acid and the following mono-hydric or poly-hydric alcohol methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane, and mixtures thereof.

(15) Esters of β-(3,5-dicyclohexyl-4-hydroxyphenyl)propionic acid and the following mono-hydric or poly-hydric alcohol methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane, and mixtures thereof.

(16) Esters of 3,5-di-t-butyl-4-hydroxyphenylacetic acid and the following mono-hydric or poly-hydric alcohol methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane, and mixtures thereof.

(17) Amides of β-(3,5-di-t-butyl-4-hydroxyphenyl)propionic acid

N,N'-bis[3-(3',5'-di-t-butyl-4'-hydroxyphenyl)propionyl]hydrazine,

N,N'-bis[3-(3',5'-di-t-butyl-4'-hydroxyphenyl)propionyl] hexamethylenediamine,

N,N'-bis[3-(3',5'-di-t-butyl-4'-hydroxyphenyl)propionyl]trimethylenediamine, and mixtures thereof.

Particularly preferable phenol-based antioxidants include the following compounds.

The phenol-based antioxidants may be used as a mixture of two or more compounds.

2,6-di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis(4-ethyl-6-t-butylphenol), 2,2'-methylenebis[4-methyl-6-(a-methylcyclohexyl)phenol), 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol bis[3,3-bis-3'-butyl-4'-hydroxyphenyl butylate], 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, 2,4,6-tris(3,5-di-t-butyl-4-phenoxy)-1,3,5-triazine, tris(4-t-butyl-3-hydroxy-2,6-dimethylbenzyl)isocyanurate, bis(3,5-di-t-butyl-4-hydroxybenzyl)isocyanurate, tris[2-(3',5'-di-t-butyl-4'-hydroxycinnamoyloxy)ethyl]isocyanurate, diethyl-3,5-di-t-butyl-4-hydroxybenzyl phosphonate, di-n-octadecyl-3,5-di-t-butyl-4-hydroxybenzyl phosphonate, calcium salt of 3,5-di-t-butyl-4-hydroxybenzyl phosphonate monoester, n-octadecyl 3-(3,5-di-t-butyl-4-hydroxyphenyl)propionate, neopentanetatrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyl-4-hydroxy-3-methylcinnamate), 3,9-bis[2-(3-(3-t-butyl-4-hydroxy-5-methylphenyl)propionyloxy)-1,1-dimethylethyl]-2,4,8,10-tetraoxaspiro[5•5]undecane, N,N'-bis[3-(3',5'-di-t-butyl-4'-hydroxyphenyl)propionyl]hydrazine, N,N'-bis[3-(3',5'-di-t-butyl-4'-hydroxyphenyl)propionyl]hexamethylenediamine and the like.

As the phosphorus-based antioxidant, the following compounds are mentioned, and these may be used as a mixture of two or more compounds.

tris(nonylphenyl)phosphite, tris(2,4-di-t-butylphenyl) phosphite, distearylpentaerythritol diphosphite, bis(2,4-di-t-butylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, tetrakis(2,4-di-t-butylphenyl)-4,4'-diphenylene diphosphite, 2,2'-methylenebis(4,6-di-t-butylphenyl)2-ethylhexyl phosphite, 2,2'-ethylidenebis(4,6-di-t-butylphenyl)fluoro phosphite, bis(2,4-di-t-butyl-6-methylphenyl)ethyl phosphite, 2-(2,4,6-tri-t-butylphenyl)-5-ethyl-5-butyl-1,3,2-oxaphosphorynane, 2,2',2"-nitrilo[triethyl-tris(3,3',5,5'-tetra-t-butyl-1,1'-biphenyl-2,2'-diyl)phosphate, 2,4,8,10-tetra-t-butyl-6-[3-(3-methyl-4-hydroxy-5-t-butylphenyl)propoxy]dibenzo[d,f][1,3,2]dioxa phosphepine, bis(2,4-dicumylphenyl)pentaerythritol diphosphite and the like.

The sulfur-based antioxidant includes, for example, the following compounds, and these may be used as a mixture of two or more compounds.

dilauryl 3,3'-thiodipropionate, tridecyl 3,3'-thiodipropionate, dimyristyl 3,3'-thiodipropionate, distearyl 3,3'-thiodipropionate, laurylstearyl 3,3'-thiodipropionate, neopentanetetrayltetrakis (3-lauryl thiopropionate) and the like.

The benzofuranones include 5,7-di-t-butyl-3-(3,4-dimethylphenyl)-3H-benzofuran-2-one and the like.

The ultraviolet absorber includes, for example, the following compounds, and these may be used as a mixture of two or more compounds.

(1) Salicylate Derivatives phenyl salicylate, 4-t-butylphenyl salicylate, 2,4-di-t-butylphenyl 3',5'-di-t-butyl-4'-hydroxy benzoate, 4-t-octylphenyl salicylate, bis(4-t-butylbenzoyl)resorcinol, benzoyl resorcinol, hexadecyl 3',5'-di-t-butyl-4'-hydroxy benzoate, octadecy, 3',5'-di-t-butyl-4'-hydroxy benzoate, 2-methyl-4,6-di-t-butylphenyl 3',5'-di-t-butyl-4'-hydroxy benzoate, and mixtures thereof and the like.

(2) 2-hydroxybenzophenone Derivatives 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone, and mixtures thereof and the like.

(3) 2-(2'-hydroxyphenyl)benzotriazole, 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole, 2-[2'-hydroxy-3',5'-bis(a,a-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl-5'-[2-(2-ethylhexyloxy)carbonylethyl]-2'-hydroxyphenyl]-5-chlorobenzotriazole, 2-[3'-t-butyl-2'-hydroxy-5'-(2-methoxycarbonylethyl)phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl]benzotriazole, 2-[3'-t-butyl-2'-hydroxy-5'-[2-(2-ethylhexyloxy)carbonylethyl]phenyl]benzotriazole, 2-[2-hydroxy-3-(3,4,5,6-tetrahydrophthalimidemethyl)-5-methylphenyl]benzotriazole, 2-(3,5-di-t-butyl-2-hydroxyphenyl)-5-chlorobenzotriazole, mixture of 2-(3'- dodecyl-2'-hydroxy-5'-methylphenyl)benzotriazole and 2-[3'-t-butyl-2'-hydroxy-5'-(2-isooctyloxycarbonylethyl) phenyl]benzotriazole, 2,2'-methylenebis[6-(2H-benzotriazole-2-yl)-4-(1,1,3,3-tetramethylbutyl)phenol, 2,2'-methylenebis[4-t-butyl-6-(2H-benzotriazole-2-yl)phenol], condensate of poly(3 to 11)(ethylene glycol) and 2-[3'-t-butyl-2'-hydroxy-5'-(2-methoxycarbonylethyl)phenyl]benzotriazole, condensate of poly(3 to 11) (ethylene glycol) and methyl 3-[(2H-benzotriazol-2-yl)-5-t-butyl-4-hydroxyphenyl]propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl]propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenyl] propionic acid, and mixtures thereof and the like.

(4) 2-(2-hydroxyphenyl)-1,3,5-triazines 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-[2,4-dihydroxyphenyl-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine, 2-(4,6-diphenyl-1,3,5-triazin-2-yl)-5-[(hexyl)oxy]-phenol, and mixtures thereof and the like.

(5) Malonates dimethyl p-methoxybenzylidenemalonate, phostabine B-CAPXP, and mixtures thereof and the like.

Particularly preferable ultraviolet absorbers include the following compounds, and these may be used as a mixture of two or more compounds.

phenyl salicylate, 4-t-butylphenyl salicylate, 2,4-di-t-butylphenyl 3',5'-di-t-butyl-4'-hydroxy benzoate, 4-t-octylphenyl salicylate, 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone, 2-(2-hydroxy-5-methyphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole, 2-[2'-hydroxy-3',5'-bis(a,a-dimethylbenzyl)phenyl]-2H-benzotriazole 2,2'-methylenebis[6-(2H-benzotriazol-2-yl)-4-(1,1,3,3-tetramethylbutyl)phenol, 2-(2-hydroxy-4-octyloxyphenyl)-4,6-bis(2,4-dimethylphenyl)-1,3,5-triazine, 2-(4,6-diphenyl-1,3,5-triazin-2-yl)-5-[(hexyl)oxy]-phenol, dimethyl p-methoxybenzylidenemalonate, phosbitane B-CAPXP and the like.

The photo-stabilizer includes, for example, the following compounds.

(1) Hindered Amine-Based Photo-Stabilizer bis(2,2,6,6-tetramethyl-4-piperidyl)sevacate, bis(2,2,6,6-tetramethyl-4-piperidyl)succinate, bis(1,2,2,6,6-pentamethyl-4-piperidyl)sevacate, bis(N-octoxy-2,2,6,6-tetramethyl-4-piperidyl)sevacate, bis(N-benzyloxy-2,2,6,6-tetramethyl-4-piperidyl)sevacate, bis(N-cyclohexyloxy-2,2,6,6-tetramethyl-4-piperidyl)sevacate, bis(1,2,2,6,6-pentamethyl-4-piperidyl) 2-(3,5-di-t-butyl-4-hydroxybenzyl)-2-butyl malonate, bis(1-acloyl-2,2,6,6-tetramethyl-4-piperidyl) 2,2-bis(3,5-di-t-butyl-4-hydroxybenzyl)-2-butyl malonate, bis(1,2,2,6,6-pentamethyl-4-piperidyldecane diolate, 2,2,6,6-tetramethyl-4-piperidinyl methacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetrakis(2,2,6,6-tetramethyl-4-piperidyl) 1,2,3,4-butanetetracarboxylate, tetrakis(1,2,2,6,6-pentamethyl-4-piperidyl) 1,2,3,4-butanetetracarboxylate, mixed esterified compound of 1,2,3,4-butanetetracarboxylic acid and 1,2,2,6,6-pentamethyl-4-piperidinol and 1-tridecanol, mixed esterified compound of 1,2,3,4-butanetetracarboxylic acid and 2,2,6,6-tetramethyl-4-piperidinol and 1-tridecanol, mixed esterified compound of 1,2,3,4-butanetetracarboxylic acid and 1,2,2,6,6-pentamethyl-4-piperidinol and 3,9-bis(2-hydroxy-1,1-dimethylethyl)-2,4,8,10-tetraoxaspiro[5•5]undecane, mixed esterified compound of 1,2,3,4-butanetetracarboxylic acid and 2,2,6,6-tetramethyl-4-piperidinol and 3,9-bis(2-hydroxy-1,1-dimethylethyl)-2,4,8,10-tetraoxaspiro [5•5]undecane, polycondensate of dimethyl succinate and 1-(2-hydroxyethyl)-4-hydroxy-2,2,6,6-tetramethylpiperidine; poly[(6-morpholino-1,3,5-triazin-2,4-diyl)((2,2,6,6-tetramethyl-4-piperidyl)imino)hexamethylene((2,2,6,6-tetramethyl-4-piperidyl)imino)], poly[(6-(1,1,3,3-tetramethylbutyl)imino-1,3,5-triazin-2,4-diyl((2,2,6,6-tetramethyl-4-piperidyl)imino)hexamethylene((2,2,6,6-tetramethyl-4-piperidyl)imino)), polycondensate of N,N'-bis (2,2,6,6-tetramethyl-4-piperidyl)hexamethylenediamine and 1,2-dibromoethane; N,N',4,7-tetrakis[4,6-bis(N-butyl-N-(2,2,6,6-tetramethyl-4-piperidyl)amino)-1,3,5-triazin-2-yl]-4,7-diazadecane-1,10-diamine, N,N',4-tris[4,6-bis(N-butyl-N-(2,2,6,6-tetramethyl-4-piperidyl)amino)-1,3,5-triazin-2-yl]-4,7-diazadecane-1,10-diamine, N,N',4,7-tetrakis[4,6-bis(N-butyl-N-(1,2,2,6,6-pentamethyl-4-piperidyl)amino)-1,3,5-triazin-2-yl]-4,7-diazadecane-1,10-diamine, N,N',4-tris[4,6-bis(N-butyl-N-(1,2,2,6,6-pentamethyl-4-piperidyl)amino)-1,3,5-triazin-2-yl]-4,7-diazadecane-1,10-diamine, and mixtures thereof and the like.

(2) Acrylate-Based Photo-Stabilizers ethyl a-cyano-β,β-diphenyl acrylate, isooctyl a-cyano-β,β-diphenyl acrylate, methyl a-carbomethoxy cinnamate, methyl a-cyano-β-methyl-p-methoxy cinnamate, butyl a-cyano-β-methyl-p-methoxy cinnamate, methyl a-carboxyl-p-methoxy cinnamate, N-(β-carbomethoxy-β-cyanovinyl)-2-methylindoline, and mixtures thereof and the like.

(3) Nickel-Based Photo-Stabilizers nickel complex of 2,2'-thiobis-[4-(1,1,3,3-tetramethylbutyl)phenol], nickeldibutyl dithiocarbamate, nickel salt of monoalkyl ester, nickel complex of ketoxime, and mixtures thereof and the like.

(4) Oxamide-Based Photo-Stabilizers 4,4'-dioctyloxyoxanilide, 2,2'-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-5-t-butyl-2'-ethoxyanilide, 2-ethoxy-5,4'-di-t-butyl-2'-ethyloxanilide, and mixtures thereof and the like.

The hydroxyamine includes, for example, N,N-dibenzylhydroxyamine, N,N-diethylhydroxyamine, N,N-dioctylhydroxyamine, N,N-dilaurylhydroxyamine, N,N-ditetradecylhydroxyamine, N,N-dihexadecylhydroxyamine, N,N-dioctadecylhydroxyamine, N-hexadecyl-N-octadecylhydroxyamine, N-heptadecyl-N-octadecylhydroxyamine, and mixtures thereof and the like.

The metal inactivating agent includes, for example, the following compounds.

N,N'-diphenyloxamide, N-salicylal-N'-salicyloylhydrazine, N,N'-bis(salicyloyl)hydrazine, N,N'-bis(3,5-di-t-butyl-4-hydroxyphenylpropionyl)hydrazine, 3-salicyloylamino-1,2,4-triazole, bis(benzylidene)oxalyldihydrazide, oxanilide, isophthaloyldihydrazine, sevacoylbisphenylhydrazide, N,N'-bis(salicyloyl)oxalyldihydrazide, N,N'-bis(salicyloyl)thiopropionyldihydrazide, and mixtures thereof and the like.

The peroxide scavenger includes, for example, ester of β-thiodipropionic acid, mercaptobenzoimidazole, zinc salt of 2-mercaptobenzoimidazole, zinc salt of dibutyldithiocarbamic acid, dioctadecyl disulfide, pentaerythritoltetrakis(β-dodecylmercapto)propionate, and mixtures thereof and the like.

The polyamide stabilizer includes, for example, iodides, or copper or manganese salts of phosphorus compounds, and mixtures thereof and the like.

The neutralizer includes, for example, calcium stearate, zinc stearate, magnesium stearate, hydrotalcite (basic magnesium•aluminum•hydroxy•carbonate•hydrate), melamine, amine, polyamide, polyurethane, and mixtures thereof and the like.

The lubricant includes, for example, aliphatic hydrocarbons such as paraffin, wax and the like, higher aliphatic acids having 8 to 22 carbon atoms, higher aliphatic acid metal salts having 8 to 22 carbon atoms (salt of Al, Ca, Mg and Zn), aliphatic alcohols having 8 to 22 carbon atoms, polyglycol, esters of higher aliphatic acids having 4 to 22 carbon atoms and aliphatic monovalent alcohols, higher aliphatic amides having 8 to 22 carbon atoms, silicone oil, rosin derivatives and the like.

The nucleating agent includes, for example, the following compounds.

sodium 2,2'-methylenebis(4,6-di-t-butylphenyl)phosphate, [phorphoric acid-2,2'-methylenebis(4,6-di-t-butylphenyl)]dihydroxyaluminum, bis[phorphoric acid-2,2'-methylenebis(4,6-di-t-butylphenyl)]hydroxyaluminum, tris[phorphoric acid-2,2'-methylenebis(4,6-di-t-butylphenyl)] aluminum, sodium bis(4-t-butylphenyl)phosphate, benzoic acid metal salts such as sodium benzoate and the like, aluminum p-t-butyl benzoate, 1,3:2,4-bis(O-benzylidene)sorbitol, 1,3:2,4-bis(O-methylbenzylidene)sorbitol, 1,3:2,4-bis(O-ethylbenzylidene)sorbitol, 1,3-O-3,4-dimethylbenzylidene-2,4-O-benzylidenesorbitol, 1,3-O-benzylidene-2,4-O-3,4-dimethylbenzylidenesorbitol, 1,3:2,4-bis(O-3,4-dimethylbenzylidene)sorbitol, 1,3-O-p-chlorobenzylidene-2,4-O-3,4-dimethylbenzylidenesorbitol, 1,3-O-3,4-dimethylbenzylidene-2,4-O-p-chlorobenzylidenesorbitol, 1,3:2,4-bis(O-p-chlorobenzylidene)sorbitol, and mixtures thereof and the like.

The filler includes, for example, glass fiber, carbon fiber, alumina fiber, carbon black, graphite, titanium oxide, silica, talc, mica, calcium carbonate, calcium sulfate, barium carbonate, oxysulfate, tin oxide, alumina, kaolin, silicon carbide, metal powder, and mixtures thereof and the like.

The antistatic agent includes, for example, polyether ester amide, glycerin monostearate, ammonium dodecylbenzenesulfonate, phosphonium dodecylbenzenesulfonate, anhydrous maleic monoglyceride, anhydrous maleic diglyceride, carbon, graphite, metal powder and the like.

Typical examples of the dye include CI. Solvent Violet 13, Macrolex Violet B and Tetrazole Blue-RLS of Beyer, and the like.

The flame retardant includes polycarbonate type flame retardant of halogenated bisphenol A, organic salt-based flame retardant, aromatic phosphate-based flame retardant or halogenated aromatic phosphate-based flame retardant, and mixtures thereof and the like.

The polycarbonate type flame retardant of halogenated bisphenol A includes polycarbonate type flame retardant of tetrabromobisphenol A, copolymer polycarbonate type flame retardant of tetrabromobisphenol A and bisphenol A.

The organic salt-based flame retardant includes dipotassium diphenylsulfone-3,3'-disulfonate, potassium diphenylsulfone-3-sulfonate, sodium 2,4,5-trichlorobenzenesulfonate, potassium 2,4,5-trichlorobenzenesulfonate, potassium bis(2,6-dibromo-4-cumylphenyl)phosphate, sodium bis(4-cumylphenyl)phosphate, bis(p-toluenesulfone) imidepotassium, bis(diphenylphosphoric acid)imidepotassium, potassium bis(2,4,6-tribromophenyl)phosphate, potassium bis(2,4-dibromophenyl)phosphate, potassium bis(4-bromophenyl)phosphate, potassium diphenylphosphate, sodium diphenylphosphate, potassium perfluorobutanesulfonate, sodium laurylsulfate, potassium laurylsulfate, sodium hexadecylsulfate, potassium hexadecylsulfate and the like.

The halogenated aromatic phosphate-type flame retardant includes tris(2,4,6-tribromophenyl)phosphate, tris(2,4-dibromophenyl)phosphate or tris(4-bromophenyl)phosphate and the like.

The aromatic phosphate-type flame retardant includes triphenyl phosphate, tris(2,6-xylyl)phosphate, tetrakis(2,6-xylyl)resorcin diphosphate, tetrakis(2,6-xylyl)hydroquinone diphosphate, tetrakis(2,6-xylyl)-4,4'-biphenol diphosphate, tetraphenylresocrin diphosphate, tetraphenylhydroquinone diphosphate, tetraphenyl-4,4'-biphenol diphosphate, aromatic polyphosphates of which aromatic ring feeding source is resorcin and phenol and containing no phenolic OH group, aromatic polyphosphates of which aromatic ring feeding source is resorcin and phenol and containing a phenolic OH group, aromatic polyphosphates of which aromatic ring feeding source is hydroquinone and phenol and containing no phenolic OH group, aromatic polyphosphates of which aromatic ring feeding source is hydroquinone and phenol and containing a phenolic OH group, aromatic polyphosphates of which aromatic ring feeding source is bisphenol A and phenol, aromatic polyphosphates of which aromatic ring feeding source is tetrabromobisphenol A and phenol, aromatic polyphosphates of which aromatic ring feeding source is resorcin and 2,6-xylenol, aromatic polyphosphates of which aromatic source is hydroquinone and 2,6-xylenol, aromatic polyphosphates of which aromatic ring feeding source is bisphenol A and 2,6-xylenol, aromatic polyphosphates of which aromatic ring feeding source is tetrabromobisphenol A and 2,6-xylenol, and the like.

The releasing agent includes, for example, esters of alcohols and fatty acids such as esters of mono-hydric alcohols and fatty acids, partial esters of poly-hydric alcohols and fatty acids, whole esters of poly-hydric alcohols and fatty acids, and the like.

The ester of a mono-hydric alcohol and an unsaturated fatty acid includes stearyl stearate, palmityl palmitate, butyl stearate, methyl laurate, isopropyl palmitate and the like.

The ester of a mono-hydric alcohol and an unsaturated fatty acid is preferably stearyl stearate.

The partial ester or whole ester of a poly-hydric alcohol and an unsaturated fatty acid includes stearic monoglyceride, stearic diglyceride, stearic triglyceride, stearic monosorbitate, behenic monoglyceride, pentaerythritol monostearate, pentaerythritol tetrastearate, pentaerythritol tetrapelargonate, propylene glycol monostearate, biphenyl biphenate, sorbitan monostearate, 2-ethylhexyl stearate, whole esters or partial esters of dipentaerythritol hexastearate and the like.

Of these esters, steric monoglyceride, stearic triglyceride, pentaerythritol tetrastearate, and a mixture of stearic triglyceride and stearyl stearate, are preferably used.

The acid value of the above-mentioned fatty ester is preferably 3 or less, more preferably 2 or less.

In the case of stearic monoglyceride, it is preferable that the acid value is 1.5 or less and the purity is 95 wt % or more, and it is particularly preferable that the acid value is 1.2 or less and the purity is 98 wt % or more.

As the releasing agent other than the above-mentioned ester, olefin-based waxes, olefin-based waxes containing a carboxyl group and/or carboxylic anhydride group, silicone oil, organopolysiloxane, paraffin wax, bees wax and the like are mentioned.

The organic peroxide includes, for example, alkyl peroxides such as dicumyl peroxide, di-t-butyl peroxide, di-t-butylcumyl peroxide, 2,5-dimethyl-2,5-di(t-butylperoxy)hexane, 2,5-dimethyl-2,5-di-(t-butylperoxy)hexene, 1,3-bis(t-butylperoxyisopropyl)benzene, 3,6,9-triethyl-3,6,9-trimethyl-1,4,7-triperoxynonane and the like;

diacyl peroxides such as benzoyl peroxide, lauroyl peroxide, decanoyl peroxide and the like;

peroxy esters such as 1,1,3,3-tetramethylbutylperoxy neodecanate, t-butylperoxy neodecanate, a-cumylperoxy neodecanate, t-butyl neoheptanate, t-butylperoxy pivalate, t-hexylperoxy pivalate, 1,1,3,3-tetramethylbutylperoxy-2-ethyl hexanate, t-amylperoxy-2-ethyl hexanate, t-butylperoxy isobutylate, di-t-butylperoxyhexahydro terephthalate, t-amylperoxy-3,5,5-trimethyl hexanate, t-butylperoxy acetate, t-butylperoxy benzoate, di-t-butylperoxytrimethyl adipate and the like;

peroxy carbonates such as di-3-methoxybutylperoxy dicarbonate, di(2-ethylhexyl)peroxy dicarbonate, diisopropylperoxy carbonate, t-butylperoxyisopropyl carbonate, di(4-t-butylcylohexyl)peroxy dicarbonate, dicetylperoxy dicarbonate, dimyristylperoxy dicarbonate and the like.

When the organic material is a polycarbonate, the processing temperature is usually 250 to 400° C., preferably 280 to 360° C., further preferably 300 to 350° C.

The organic material composition of the present invention containing a polycarbonate as the organic material can provide a product excellent in appearance in molding, for example, electric appliance housings, optical lenses, illumination covers, disks such as CD, DVD and the like, automobile parts such as a head lamp lens cover and the like, sheet-shaped molded articles such as window panes, carport roofs and the like, since thermal decomposition of the polycarbonate is prevented.

In the present invention, when an organic silicon compound (I) and, other additives to be used according to demands are added to the organic material, it is recommendable to give a uniform composition, and the method and apparatus for this are not particularly restricted.

For example, when an organic silicon compound (I) and, other additives to be used according to demands are added in a process of producing the organic material (polymerization process), the organic silicon compound (I) and, other additives to be used according to demands may be added, in the form of solution or dispersion, or in the melted condition, to polymer liquid during polymerization or directly after polymerization.

When an organic silicon compound (I) and, other additives to be used according to demands are added in a heating process after volatilization, the organic silicon compound and, other additives to be used according to demands may be dry-blended directly with the organic material, or may be mixed with the organic material using a mixer such as Henschel mixer and the like.

Further, it is also possible that an organic silicon compound (I) and, other additives to be used according to demands are compounded in the form of master batch into the organic material.

EXAMPLES

The present invention will be illustrated further in detail by the following examples and the like, but the present invention is not limited to these examples.

Example 1

Production of
1,1,3,3-tetrakis(2-methoxyphenyl)disiloxane
(Hereinafter, Referred to as Compound 1)

Into a four-necked flask (i) was charged 3.6 g of magnesium, 50 ml of tetrahydrofuran and a small amount of bromine under nitrogen flow, and mixed liquid of 25 g of 2-bromoanisole and 50 ml of tetrahydrofuran was dropped while stirring. After completion of dropping, the mixture was thermally insulated at 70° C. for 3 hours. The resultant reaction mixture was dropped into a mixture of 9 g of trichlorosilane and 50 ml of tetrahydrofuran charged in a four-necked flask (ii) under ice cooling. After completion of dropping, the mixture was stirred for 18 hours at room temperature.

The resultant reaction mixture was washed with saturated saline three times, then, the organic phase was dried over anhydrous magnesium sulfate, then, magnesium sulfate was filtrated off. From the resultant filtrate, a solvent was distilled off. The residue after distillation was re-crystallized from tetrahydrofuran, to obtain 5.6 g of compound 1.

<Mass spectrometry of compound 1 (FD-MS)> m/z=502
<1H-NMR of compound 1 (heavy tetrahydrofuran)> d3.52 (s, 12H), 5.63 (s, 2H), 6.75 (d, 4H), 6.82 (t, 4H), 7.27 (t, 4H), 7.40 (m, 4H)

Example 2

Production of
1,1,3,3-tetrakis(2-methylphenyl)disiloxane
(Hereinafter, Referred to as Compound 2)

Into a four-necked flask (iii) was charged 6.8 g of trichlorosilane and 50 ml of tetrahydrofuran. In to the mixture, 100 ml of a tetrahydrofuran solution of o-tolylmagnesium bromide (containing 1.0 mmol of o-tolylmagnesium bromide per 1 ml) was dropped at 0° C. under nitrogen flow. After completion of dropping, the mixture was stirred at room temperature for 5 hours. After completion of stirring, 50 g of water and 100 g of toluene were added, and the mixture was thermally insulated at 113° C. for 5 hours. After completion of thermal insulation, 30 g of 1N-hydrochloric acid was added, and the mixture was allowed to stand at room temperature overnight. After standing overnight, the solution was heated up to 111° C. and thermally insulated for 1 hour at the same temperature. Then, the solution was washed with saturated saline, then, the resulting organic phase was dried over anhydrous magnesium sulfate.

Anhydrous magnesium sulfate was filtrated off, then, the resulting filtrate was distilled off, to obtain toluene of low boiling point and a fraction of high boiling point. The resulting fraction of high boiling point was re-crystallized from ethanol, to obtain 1.4 g of compound 2.

<Mass spectrometry of compound 2 (FD-MS)> m/z=438
<1H-NMR of compound 2 (CDCl$_3$)> d2.22 to 2.26 (m, 12H), 5.75 (s, 2H), 7.07 to 7.14 (m, 8H), 7.26 to 7.29 (m, 4H), 7.54 (d, 4H)

Example 3

Production of 1,1,3,3-tetrakis(2-methyl-4-methoxyphenyl)disiloxane (Hereinafter, Referred to as Compound 3)

Into a four-necked flask (iv) was charged 1.6 g of magnesium, 50 ml of tetrahydrofuran and a small amount of bromine under nitrogen flow. Then, mixed liquid of 12 g of 2-bromo-5-methoxytoluene and 50 ml of tetrahydrofuran was dropped while stirring. After completion of dropping, the mixture was thermally insulated at 70° C. for 2 hours. A mixture of 3.2 g of trichlorosilane and 50 ml of tetrahydrofuran was charged into a four-necked flask (v), and into this mixture was dropped at −30° C. the above-mentioned reaction solution thermally insulated for 2 hours. After completion of dropping, the mixture was stirred for 1 hour at room temperature. Into the resultant reaction mixture was dropped saturated saline at −30° C., and after completion of dropping, the mixture was stirred at room temperature for 12 hours. The resultant organic phase washed with saturated saline twice, then, the resultant organic phase was dried over anhydrous magnesium sulfate. Anhydrous magnesium sulfate was filtrated off. From the resultant filtrate, a solvent was distilled off. The residue after distillation was re-crystallized from a mixed solvent of tetrahydrofuran/n-hexane, to obtain 0.5 g of compound 3.

<Mass spectrometry of compound 3 (FD-MS)> m/z=558
<1H-NMR of compound 3 (CDCl3)> d2.36 (s, 12H), 3.80 (s, 12H), 5.62 (s, 2H), 6.73 to 6.75 (m, 8H), 7.48 (d, 4H)

Example 4

Production of 1,1,3,3-tetrakis(2,4-dimethoxyphenyl)disiloxane (Hereinafter, Referred to as Compound 4)

Into a four-necked flask (vi) was charged 3.1 g of magnesium and 20 ml of tetrahydrofuran under nitrogen flow. Into the mixture was dropped mixed liquid of 25 g of 1-bromo-2,4-dimethoxybenzene and 80 ml of tetrahydrofuran while stirring. After completion of dropping, the mixture was thermally insulated for 2 hours under reflux. Into a four-necked flask (vii) was charged 9.5 g of triethoxysilane and 40 ml of tetrahydrofuran. Into this mixture was dropped under ice cooling the above-mentioned reaction solution thermally insulated for 2 hours under reflux, and after completion of dropping, the mixture was stirred for 2 hours at 80° C. The resultant reaction mixture was washed with 100 ml of ammonium chloride water and saturated saline sequentially. The organic phase after washing was dried over anhydrous magnesium sulfate. Anhydrous magnesium sulfate was filtrated off, then, to the resultant organic phase was added silica gel for decoloration. The organic phase after decoloration was concentrated, to obtain 16.7 g of bis(2,4-dimethoxyphenyl) ethoxysilane. To the above-mentioned bis(2,4-dimethoxyphenyl)ethoxysilane was added at 0° C. 50 ml tetrahydrofuran and 50 ml of 1N-hydrochloric acid. Then, 100 g of toluene was added and extraction was performed. The organic phase was washed with saturated saline twice. To the organic phase after washing was anhydrous magnesium sulfate and dried. Anhydrous magnesium sulfate was filtrated, then, the filtrate was concentrated and a solvent was distilled off. The residue after solvent distillation was thermally insulated at 155° C. for 2 hours, then, further thermally insulated at 160° C. for 5 hours. Thereafter, a component of low boiling point was distilled off at 230° C. To the reaction mixture after distilling off a component of low boiling point was added a mixed solution of 2-propanol/toluene to cause deposition of a crystal, obtaining 5.3 g of compound 4.

<Mass spectrometry of compound 4 (FD-MS)> m/z=622
<1H-NMR of compound 4 (CDCl3)> d3.55 (s, 12H), 3.77 (s, 12H), 5.54 (s, 2H), 6.29 (d, 4H), 6.41 to 6.43 (m, 4H), 7.32 (d, 4H)

Example 5

Production of 1,1,3,3-tetrakis(4-methoxyphenyl)disiloxane (Hereinafter, Referred to as Compound 5)

Into a four-necked flask (viii) was charged 3.6 g of magnesium, 20 ml of tetrahydrofuran and a small amount of bromine under nitrogen flow, and mixed liquid of 25 g of 4-bromoanisole and 80 ml of tetrahydrofuran was dropped while stirring. After completion of dropping, the mixture was thermally insulated at 70° C. for 3 hours. Into a four-necked flask (ix) was charged a mixture of 11.0 g of triethoxysilane and 40 ml of tetrahydrofuran, and the above-mentioned reaction mixture obtained by thermally insulated at 70° C. for 3 hours was dropped under ice cooling. After completion of dropping, the mixture was stirred for 18 hours at room temperature. The resultant reaction mixture was washed with saturated saline three times, then, the organic phase was dried over anhydrous magnesium sulfate. Anhydrous magnesium sulfate was filtrated off, then, the filtrate was concentrated and a solvent was distilled off. To the resultant residue was added a mixed solution of ethanol/toluene, to cause deposition of a crystal. Then, the deposited crystal was re-crystallized from the mixed solvent of toluene/n-hexane, to obtain 7.8 g of compound 5.

<Mass spectrometry of compound 5 (FD-MS)> m/z=502
<1H-NMR of compound 5 (CDCl3)> d3.78 (s, 12H), 5.54 (s, 2H), 6.87 (d, 8H), 7.46 (d, 8H)

Example 6

Production of 1,1,3,3-tetrakis(2,5-dimethoxyphenyl)disiloxane (Hereinafter, Referred to as Compound 6)

Into a four-necked flask (x) was charged 1.5 g of magnesium, 50 ml of tetrahydrofuran and a small amount of bromine under nitrogen flow. Then, mixed liquid of 12 g of 1-bromo-2,5-dimethoxybenzene and 50 ml of tetrahydrofuran was dropped while stirring. After completion of dropping, the mixture was thermally insulated at 70° C. for 2 hours. Into a four-necked flask (xi) was charged 3.4 g of trichlorosilane and 50 ml of tetrahydrofuran, and the above-mentioned reaction solution thermally insulated at 70° C. for 2 hours was dropped −30° C. After completion of dropping, the mixture was stirred for 1 hour at room temperature. The resultant reaction mixture was washed with saturated saline three times, then, the resultant organic phase was dried over anhydrous magnesium sulfate. Anhydrous magnesium sulfate was filtrated off, then, the filtrate was concentrated and a solvent was distilled off. The concentration residue was re-crystallized from a mixed solvent of tetrahydrofuran/hexane, to obtain 2.2 g of compound 6.

<Mass spectrometry of compound 6 (FD-MS)> m/z=622
<1H-NMR of compound 6 (CDCl3)> δ3.54 (s, 12H), 3.64 (s, 12H), 5.61 (s, 2H), 6.67-6.68 (m, 4H), 6.83-6.85 (m, 4H), 7.03 (m, 4H)

Example 7 and Comparative Example 1

To 100 parts by weight of polycarbonate (Calibre manufactured by Sumitomo Dow) was added 0.025 parts by weight of compound 1, and the mixture was melt-kneaded at 340° C. using a 30 mmφ single screw extruder, to obtain a pellet of a polycarbonate resin composition. This pellet was retained at 360° C. for 10 minutes, then, molded using an injection molding machine, to obtain a sheet (Example 7). The same operation as in Example 7 was carried out except that compound 1 was not added, to obtain a sheet (Comparative Example 1). Color difference (ΔYI) between the two sheets obtained in Example 7 and Comparative Example 1 was measured by a color difference meter. Measurement results of relative values when the ΔYI value obtained in Comparative Example 2 is 1 are shown in Table 1. Smaller ΔYI value shows less coloration and less thermal degradation in retaining.

Examples 8 to 12

Sheets were obtained in the same manner as in Example 7 except that compounds 2, 3, 4, 5 and 6 were added instead of compound 1, each in the same amount as that of compound 1, to 100 parts by weight of the polycarbonate used in Example 7.

Measurement results of color difference of the sheets obtained in Examples 8 to 12 (measured, using the sheet obtained in Comparative Example 1 as a control) are shown in Table 1 together with the measurement result of the sheet of Example 7.

Comparative Example 2

A sheet was obtained in the same manner as in Example 7 except that 0.025 parts by weight of triphenylsilane was added instead of compound 1, to 100 parts by weight of the polycarbonate used in Example 7.

The color difference of this sheet was measured in the same manner as in Example 7.

The measurement result is shown in Table 1.

TABLE 1

| | Example Number | | | | | | |
|---|---|---|---|---|---|---|---|
| | Ex. 7 | Ex. 8 | Ex. 9 | Ex. 10 | Ex. 11 | Ex. 12 | Comparative Example 2 |
| Compound | 1 | 2 | 3 | 4 | 5 | 6 | Triphenyl-silane |
| Color Difference ΔYI | −9 | −6 | −10 | −11 | −9 | −7 | 1 |

Examples 13 to 18

To 100 parts by weight of polycarbonate (Calibre manufactured by Sumitomo Dow) was added 0.025 parts by weight of compound 1 and 0.1 part by weight of 2-(2'-hydroxy-5'-t-octylphenyl)benzotriazole, and the mixture was melt-kneaded at 340° C. using a 30 mmφ single screw extruder, to obtain a pellet of a polycarbonate resin composition. This pellet was molded using an injection molding machine at 340° C., to obtain a sheet (Example 13).

A sheet was obtained by the same operation as in Example 13 except that compound 1 was not obtained (blank test).

Color difference (ΔYI) between the two sheets obtained in Example 13 and blank test was measured by a color difference meter.

Sheets were obtained in the same manner as in Example 13 except that compounds 2, 3, 4, 5 and 6 were added instead of compound 1, each in the same amount as that of compound 1.

Measurement results of color difference of the sheets obtained in Examples 14 to 18 are shown in Table 2 together with the measurement result of the sheet of Example 13.

In these examples, relative values when the ΔYI value obtained in Example 18 is −1 are shown. Smaller ΔYI value shows less coloration and less thermal degradation in retaining.

TABLE 2

| | Example Number | | | | | |
|---|---|---|---|---|---|---|
| | 13 | 14 | 15 | 16 | 17 | 18 |
| Compound No. | 1 | 2 | 3 | 4 | 5 | 6 |
| ΔYI | −1.8 | −1.5 | −2.5 | −2.0 | −1.5 | −1.0 |

Examples 19 and Comparative Example 3

To 100 parts by weight of polycarbonate (Calibre manufactured by Sumitomo Dow) was added 0.025 parts by weight of compound 1 and 0.1 part by weight of stearic monoglyceride, and the mixture was melt-kneaded at 340° C. using a 30 mmφ single screw extruder, to obtain a pellet of a polycarbonate resin composition. This pellet was retained at 360° C. for 10 minutes, then, molded using an injection molding machine, to obtain a sheet (Example 19). A sheet was obtained by the same operation as in Example 19 except that compound 1 was not obtained (Comparative Example 3).

Color difference (YI) between the sheets obtained in Example 19 and Comparative Example 3 was measured by a color difference meter, and the results are shown in Table 3.

In this example, a relative value when the YI value obtained in Comparative Example 3 is 1 is shown.

Smaller YI value shows less coloration and less thermal degradation in retaining.

TABLE 3

| | Example Number | |
|---|---|---|
| | Example 19 | Comparative Example 3 |
| YI | 0.48 | 1 |

Example 20 and Comparative Example 4

To 100 parts by weight of polycarbonate (Calibre manufactured by Sumitomo Dow) was added 0.025 parts by weight of compound 1 and 0.25 part by weight of n-octadecyl 3-(3,5-di-t-butyl-4-hydroxyphenyl) propionate, and the mixture was melt-kneaded at 340° C. using a 30 mmφ single screw extruder, to obtain a pellet of a polycarbonate resin composition. This pellet was molded using an injection molding machine at 360° C., to obtain a sheet (Example 20).

A sheet was obtained by the same operation as in Example 20 except that compound 1 was not obtained (Comparative Example 4).

Color difference (YI) between the sheets obtained in Example 20 and Comparative Example 4 was measured by a color difference meter, and the results are shown in Table 4.

In this example, a relative value when the YI value obtained in Comparative Example 4 is 1 is shown.

Smaller YI value shows less coloration and less thermal degradation in retaining.

TABLE 4

| | Example Number | |
|---|---|---|
| | Example 20 | Comparative Example 4 |
| YI | 0.78 | 1 |

Examples 21 to 23 and Comparative Example 5

To 100 parts by weight of polycarbonate (Noblen manufactured by Sumitomo Chemical Co., Ltd.) was added compound 1 and antioxidants described below in given amounts (see, Table 5 below), and the mixture was melt-kneaded at 270° C. using a 30 mmϕ single screw extruder, to obtain a pellet of a polycarbonate resin composition. This pellet was molded using an injection molding machine at 270° C., to obtain a sheet. The measurement results of color difference (YI) of the sheets are shown in Table 5.

A relative value when the YI value obtained in Comparative Example 5 is 1 is shown.

Smaller YI value shows less coloration and less thermal degradation in retaining.

Antioxidant AO-1:
Neopentanetetrayltetrakis(3,5-di-t-butyl-4-hydroxydihydrocinnamate)

Antioxidant P-1:
Tris(2,4-di-t-butylphenyl)phosphate

TABLE 5

| | Example Number | | | |
|---|---|---|---|---|
| | Example 21 | Example 22 | Example 23 | Comparative Example 5 |
| Compound 1 | 0.05 parts by weight | 0.025 parts by weight | 0.008 parts by weight | No addition |
| Antioxidant | No addition | A0-1/0.025 parts by weight | A0-1/0.021 parts by weight P-1/0.021 parts by weight | No addition |
| YI | 0.92 | 0.96 | 0.97 | 1 |

Examples 24 to 26 and Comparative Example 6

To 100 parts by weight of polycarbonate (Noblen manufactured by Sumitomo Chemical Co., Ltd.) was dry-blended 0.05 parts by weight of calcium stearate, 0.031 parts by weight of a polypropylene homopolymer impregnated with the following organic peroxide PO-1 (PO-1 concentration: 8%)(PO-1: 0.025 parts by weight), compound 1 and additives described below other than PO-1.

This mixture was melt-kneaded with heating at a set temperature of 250° C. using a 30 mmϕ single screw extruder, to obtain a pellet. The prepared pellet was further melt-kneaded with heating at a set temperature of 270° C. using a 30 mmϕ single screw extruder, to prepare a pellet, and this operation was repeated four times. A difference between MFR (M0) of the pellet prepared after processing at 250° C. and MFR (M4) of the pellet after melt kneading at 270° C. four times was designated as ΔMFR.

A relative value when the ΔMFR value obtained in Comparative Example 6 is 1 is shown in Table 6 below.

Smaller ΔMFR value shows less thermal degradation.

PO-1:
2,5-dimethyl-2,5-di-(t-butylperoxy)hexane

AO-2:
Tris(3,5-di-t-butyl-4-hydroxybenzyl)isocyanurate

HA-1:
Polycondensate of dimethyl succinate and 1-(2-hydroxyethyl)-4-hydroxy-2,2,6,6-tetramethylpiperidine

TABLE 6

| | Example Number | | | |
|---|---|---|---|---|
| | Example 24 | Example 25 | Example 26 | Comparative Example 6 |
| Compound 1 | 0.225 parts by weight | 0.11 parts by weight | 0.05 parts by weight | No addition |
| Antioxidant | No addition | A0-2/0.11 parts by weight | P0-1/0.12 parts by weight HA-1/0.05 parts by weight | No addition |
| ΔMFR | 0.79 | 0.26 | 0.16 | 1 |

Example 27 and Comparative Example 7

To 100 parts by weight of a cyclic polyolefin resin (Topas manufactured by Ticona) was dry-blended 0.3 parts by weight of compound 1.

This mixture was processed in a T die film processing machine at a set temperature of 300° C., to prepare a film (Example 27).

A film was prepared separately without adding compound 1 (Comparative Example 7).

Condition of generation of fish eye gel recognized in the resultant film was visually confirmed to find that generation of gel was suppressed in the film in Example 27 as compared with the film in Comparative Example 7.

INDUSTRIAL APPLICABILITY

The organic silicon compound of the present invention is useful as a coloration preventing agent, thermal degradation preventing agent and gel generation suppressing agent for organic materials such thermoplastic resins, natural rubber, synthetic rubber, mineral oils, lubricants, adhesives and the like.

According to the production method of the present invention, the above-mentioned organic silicon compound can be obtained easily.

Further, the organic material composition of the present invention is used for electronic appliance housings, optical lenses, building materials such as window panes, and the like.

The invention claimed is:

1. An organic material composition comprising an organic material and an organic silicon compound of formula (I):

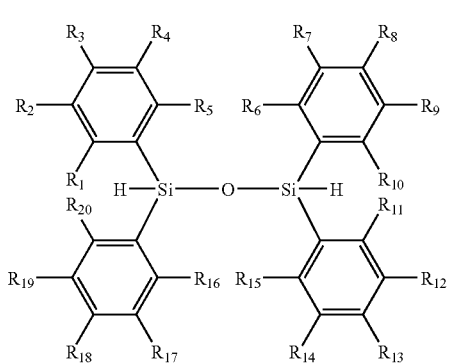

wherein
$R_1$ to $R_{20}$ each represents independently a hydrogen atom, alkyl group having 1 to 30 carbon atoms, alkoxyl group having 1 to 30 carbon atoms, alkoxyalkyl group having 2 to 30 carbon atoms, aryloxy group having 6 to 18 carbon atoms, aryl group having 6 to 18 carbon atoms, cycloalkyl group having 5 to 8 carbon atoms, alkylcycloalkyl group having 6 to 20 carbon atoms, alkylthio group having 1 to 30 carbon atoms, or dialkylamino group having 2 to 30 carbon atoms; and $R_1$ to $R_{20}$ do not all represent a hydrogen atom simultaneously, and 1 to 3 hydrogen atoms in the aryloxy group having 6 to 18 carbon atoms and the aryl group having 6 to 18 carbon atoms may be substituted by 1 to 3 substituents selected from the group consisting of alkyl groups having 1 to 30 carbon atoms, alkoxyl groups having 1 to 30 carbon atoms and alkoxyalkyl groups having 2 to 30 carbon atoms;

wherein the weight ratio of the organic material to the organic silicon compound is 100:0.0001 to 100:10; and wherein the organic material is a thermoplastic resin.

2. The organic material composition according to claim 1, wherein the thermoplastic resin is a polyolefin or engineering resin.

3. The organic material composition according to claim 2, wherein the engineering resin is a polycarbonate or polyester.

4. The organic material composition according to claim 2, wherein the engineering resin is a polycarbonate.

5. The organic material composition according to claim 2, wherein the polyolefin is polypropylene or cyclic polyolefin resin.

* * * * *